(12) United States Patent
Bushell et al.

(10) Patent No.: US 11,826,267 B2
(45) Date of Patent: Nov. 28, 2023

(54) FEMORAL TRIALLING KIT AND ASSEMBLY

(71) Applicant: DEPUY IRELAND UNLIMITED COMPANY, County Cork (IE)

(72) Inventors: Sarah Bushell, Sheffield (GB); Craig Davidson, Penrith (GB); Philippa Withers, London (GB); Duncan Young, Melbourn (GB)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 439 days.

(21) Appl. No.: 16/500,874

(22) PCT Filed: Apr. 9, 2018

(86) PCT No.: PCT/EP2018/059065
§ 371 (c)(1),
(2) Date: Oct. 4, 2019

(87) PCT Pub. No.: WO2018/189128
PCT Pub. Date: Oct. 18, 2018

(65) Prior Publication Data
US 2020/0222208 A1     Jul. 16, 2020

(30) Foreign Application Priority Data

Apr. 12, 2017 (GB) ..................... 1705917

(51) Int. Cl.
*A61F 2/34* (2006.01)
*A61F 2/36* (2006.01)
(Continued)

(52) U.S. Cl.
CPC .............. *A61F 2/4684* (2013.01); *A61F 2/34* (2013.01); *A61F 2/3609* (2013.01);
(Continued)

(58) Field of Classification Search
CPC ..... A61F 2/3609; A61F 2/4607; A61F 2/4684
See application file for complete search history.

(56) References Cited

U.S. PATENT DOCUMENTS

| 3,810,312 A | 5/1974 | Carson |
| 3,889,558 A | 6/1975 | Duncan |

(Continued)

FOREIGN PATENT DOCUMENTS

| CN | 1193899 A | 9/1998 |
| CN | 102048599 A | 5/2011 |

(Continued)

OTHER PUBLICATIONS

Lucas, David H., and Scott, Richard D; The Ranawat Sign A Specific Maneuver to Assess Component Positioning in Total Hip Arthroplasty, Journal of Orthopaedic Techniques, vol. 2, No. 2, Jun. 1994.

(Continued)

*Primary Examiner* — Nicholas W Woodall

(57) ABSTRACT

A femoral trialling kit and method for assessing acetabular cup orientation during a left hip joint surgical procedure and a right hip joint surgical procedure are described. The kit includes a trial femoral head (104, 414, 514, 614, 814) having an inner wall defining a cavity extending along a head axis and a visual alignment guide on an outer surface of the trial femoral head and a trial femoral neck (126, 412, 512, 612, 812) having a taper at a free end, the taper being receivable within the cavity. One of the taper and the inner wall has a first anti-rotation feature (684, 698) and a second anti-rotation feature (686, 700), the first anti-rotation feature and the second anti-rotation feature being inclined, and the other of the taper and the inner wall has a third anti-rotation feature (702). The trial femoral head is attachable to the trial femoral neck in a first angular configuration corresponding to a right hip joint, in which the third anti-rotation feature (Continued)

and the first anti-rotation feature engage, and a second angular configuration corresponding to a left hip joint, wherein the third anti-rotation feature and the second anti-rotation feature engage.

12 Claims, 13 Drawing Sheets

(51) Int. Cl.
*A61F 2/46* (2006.01)
*A61F 2/30* (2006.01)

(52) U.S. Cl.
CPC .......... *A61F 2002/3071* (2013.01); *A61F 2002/30331* (2013.01); *A61F 2002/30528* (2013.01); *A61F 2002/365* (2013.01); *A61F 2002/3611* (2013.01); *A61F 2002/3625* (2013.01)

(56) References Cited

U.S. PATENT DOCUMENTS

| | | | |
|---|---|---|---|
| 3,987,499 A | 10/1976 | Scharbach | |
| 4,305,394 A | 12/1981 | Bertuch, Jr. | |
| 4,601,289 A | 7/1986 | Chiarizzio | |
| 4,693,724 A | 9/1987 | Rhenter | |
| 4,957,510 A | 9/1990 | Cremascoli | |
| 4,959,066 A | 9/1990 | Dunn | |
| 4,962,155 A | 10/1990 | Fujita | |
| 4,963,155 A | 10/1990 | Lazzeri | |
| 5,002,578 A | 3/1991 | Luman | |
| 5,002,581 A | 3/1991 | Paxson | |
| 5,041,118 A | 8/1991 | Wasilewski | |
| 5,057,112 A | 10/1991 | Sherman | |
| 5,190,550 A | 3/1993 | Miller | |
| 5,342,363 A | 8/1994 | Richelsoph | |
| 5,352,231 A | 10/1994 | Brumfield | |
| 5,409,492 A | 4/1995 | Jones | |
| 5,480,451 A | 1/1996 | Grundei | |
| 5,540,687 A | 7/1996 | Fairley | |
| 5,569,263 A | 10/1996 | Hein | |
| 5,645,607 A * | 7/1997 | Hickey | A61F 2/4684 623/23.35 |
| 5,653,764 A | 8/1997 | Murphy | |
| 5,653,765 A | 8/1997 | McTighe | |
| 5,766,261 A | 6/1998 | Neal | |
| 5,858,020 A | 1/1999 | Johnson | |
| 5,876,459 A | 3/1999 | Powell | |
| 5,888,208 A | 3/1999 | Ro | |
| 5,888,211 A | 3/1999 | Sanders | |
| 5,906,644 A | 5/1999 | Powell | |
| 5,938,701 A | 8/1999 | Hiernard | |
| 6,042,611 A | 3/2000 | Noiles | |
| 6,048,365 A | 4/2000 | Burrows | |
| 6,080,162 A | 6/2000 | Dye | |
| 6,090,146 A | 7/2000 | Rozow, III | |
| 6,110,179 A | 8/2000 | Flivik | |
| 6,149,687 A | 11/2000 | Gray, Jr. | |
| 6,165,177 A | 12/2000 | Wilson | |
| 6,193,759 B1 | 2/2001 | Ro | |
| 6,197,062 B1 | 3/2001 | Fenlin | |
| 6,224,605 B1 | 5/2001 | Anderson | |
| 6,238,435 B1 | 5/2001 | Meulink | |
| 6,258,097 B1 | 7/2001 | Cook | |
| 6,330,845 B1 | 12/2001 | Meulink | |
| 6,447,518 B1 | 9/2002 | Krause | |
| 6,464,728 B1 | 10/2002 | Murray | |
| 6,491,696 B1 | 12/2002 | Kunkel | |
| 6,679,917 B2 | 1/2004 | Ek | |
| 6,702,854 B1 | 3/2004 | Cheal | |
| 6,706,072 B2 | 3/2004 | Dwyer | |
| 6,743,235 B2 | 6/2004 | Subba Rao | |
| 6,883,217 B2 | 4/2005 | Barrette | |
| 6,905,515 B1 | 6/2005 | Gilbertson | |
| 6,977,000 B2 | 12/2005 | Vanasse | |
| 7,022,141 B2 | 4/2006 | Dwyer | |
| 7,066,042 B2 | 6/2006 | Andrews | |
| 7,135,044 B2 | 11/2006 | Bassik | |
| 7,188,556 B1 | 3/2007 | Rinner | |
| 7,273,499 B2 | 9/2007 | McCleary et al. | |
| 7,297,166 B2 | 11/2007 | Dwyer | |
| 7,363,838 B2 | 4/2008 | Abdelgany | |
| 7,572,297 B2 | 8/2009 | Cheal | |
| 7,582,092 B2 | 9/2009 | Jones | |
| 7,585,329 B2 | 9/2009 | McCleary | |
| 7,608,112 B1 | 10/2009 | Kuczynski | |
| 7,641,698 B1 | 1/2010 | Gibbs | |
| 7,981,161 B2 | 7/2011 | Choi | |
| 8,048,167 B2 | 11/2011 | Dietz | |
| 8,052,758 B1 | 11/2011 | Winslow | |
| 8,449,619 B2 | 5/2013 | Metcalfe | |
| 8,663,333 B2 | 3/2014 | Metcalfe | |
| 10,980,646 B2 | 4/2021 | Grobler | |
| 11,197,764 B2 | 12/2021 | Mutchler | |
| 2002/0038148 A1 | 3/2002 | Fernandez | |
| 2002/0058999 A1 | 5/2002 | Dwyer | |
| 2002/0193882 A1 | 12/2002 | Koller | |
| 2003/0074080 A1 | 4/2003 | Murray | |
| 2003/0149487 A1 | 8/2003 | Doubler | |
| 2004/0004186 A1 | 1/2004 | Jiyan | |
| 2004/0054373 A1 | 3/2004 | Serra | |
| 2004/0064186 A1 | 4/2004 | McCleary et al. | |
| 2004/0064188 A1 | 4/2004 | Ball | |
| 2004/0073315 A1 | 4/2004 | Justin | |
| 2004/0078079 A1 | 4/2004 | Foley | |
| 2004/0122437 A1 | 6/2004 | Dwyer | |
| 2004/0122439 A1 | 6/2004 | Dwyer | |
| 2004/0122440 A1 | 6/2004 | Daniels | |
| 2004/0122525 A1 | 6/2004 | Daniels | |
| 2004/0172139 A1 | 9/2004 | Dwyer | |
| 2004/0236341 A1 | 11/2004 | Petersen | |
| 2004/0267267 A1 | 12/2004 | Daniels | |
| 2004/0267372 A1 | 12/2004 | Vanasse | |
| 2004/0267373 A1 | 12/2004 | Dwyer | |
| 2005/0033443 A1 | 2/2005 | Blatter | |
| 2005/0033444 A1 | 2/2005 | Jones | |
| 2005/0107799 A1 | 5/2005 | Graf | |
| 2005/0143828 A1 | 6/2005 | Collins | |
| 2005/0203634 A1 | 9/2005 | Bassik | |
| 2005/0245934 A1 | 11/2005 | Tuke | |
| 2005/0288792 A1 | 12/2005 | Landes | |
| 2006/0027027 A1 | 2/2006 | Serra | |
| 2006/0142871 A1 | 6/2006 | Biss | |
| 2006/0167557 A1 | 7/2006 | Terrill | |
| 2006/0217737 A1 | 9/2006 | Iversen | |
| 2006/0241625 A1 | 10/2006 | Metcalfe | |
| 2006/0260440 A1 | 11/2006 | Abdelgany | |
| 2007/0005144 A1 | 1/2007 | Leisinger | |
| 2007/0050039 A1 | 3/2007 | Dietz | |
| 2007/0100464 A1 | 5/2007 | Meulink | |
| 2007/0123908 A1 | 5/2007 | Jones | |
| 2007/0219641 A1 | 9/2007 | Dorr | |
| 2007/0233132 A1 | 10/2007 | Valla | |
| 2007/0244566 A1 | 10/2007 | Daniels | |
| 2008/0091212 A1 | 4/2008 | Dwyer | |
| 2008/0091274 A1 | 4/2008 | Murphy | |
| 2008/0133023 A1 | 6/2008 | Schlotterback | |
| 2008/0200990 A1 | 8/2008 | McTighe | |
| 2008/0262626 A1 | 10/2008 | Raugel | |
| 2009/0048682 A1 | 2/2009 | Choi | |
| 2009/0054993 A1 | 2/2009 | Le Bon | |
| 2009/0112216 A1 | 4/2009 | Leisinger | |
| 2009/0112218 A1 | 4/2009 | McCleary | |
| 2009/0187251 A1 | 7/2009 | Justin | |
| 2009/0307887 A1 | 12/2009 | Jones | |
| 2010/0100193 A1 | 4/2010 | White | |
| 2010/0241239 A1 | 9/2010 | Smith | |
| 2010/0249943 A1 | 9/2010 | Bergin | |
| 2011/0054628 A1 | 3/2011 | Banks | |
| 2011/0302760 A1 | 12/2011 | Leisinger | |
| 2012/0053698 A1 | 3/2012 | Huff | |
| 2012/0239160 A1 | 9/2012 | Belew | |
| 2012/0259338 A1 | 10/2012 | Carr | |

(56) References Cited

U.S. PATENT DOCUMENTS

| | | |
|---|---|---|
| 2012/0259423 A1 | 10/2012 | Carr |
| 2012/0265319 A1 | 10/2012 | Prybyla |
| 2012/0290099 A1 | 11/2012 | Gibson |
| 2013/0144397 A1 | 6/2013 | Smith |
| 2013/0158674 A1 | 6/2013 | Chow |
| 2013/0261762 A1 | 10/2013 | Kennedy |
| 2013/0325132 A1 | 12/2013 | Reignier |
| 2014/0276866 A1 | 9/2014 | Endsley |
| 2014/0350691 A1 | 11/2014 | Linares |
| 2015/0018961 A1 | 1/2015 | Huddle |
| 2015/0083116 A1 | 3/2015 | Zhu |
| 2016/0030200 A1* | 2/2016 | Hunt ............... A61F 2/3662 623/20.35 |
| 2016/0175116 A1 | 6/2016 | Bader |
| 2016/0193050 A1 | 7/2016 | Cappelletti |
| 2016/0262912 A1 | 9/2016 | Burnikel |
| 2017/0189206 A1* | 7/2017 | Davenport ............ A61F 2/4684 |
| 2017/0202685 A1 | 7/2017 | Rao |
| 2018/0116822 A1 | 5/2018 | Grobler |
| 2018/0303551 A1 | 10/2018 | Hopkins |
| 2019/0159904 A1* | 5/2019 | Magagnoli ............ A61F 2/3662 |
| 2019/0247063 A1 | 8/2019 | Huff |
| 2020/0222208 A1 | 7/2020 | Bushell |
| 2020/0261248 A1 | 8/2020 | Wills |
| 2020/0352742 A1 | 11/2020 | Horne |
| 2021/0093332 A1 | 4/2021 | Walker |

FOREIGN PATENT DOCUMENTS

| | | |
|---|---|---|
| CN | 106264797 A | 1/2017 |
| DE | 20114835 U1 | 1/2002 |
| DE | 202007009646 U1 | 10/2007 |
| DE | 102007032014 B3 | 10/2008 |
| EP | 1000595 A1 | 5/2000 |
| EP | 1435223 A1 | 7/2004 |
| EP | 1522284 A2 | 4/2005 |
| EP | 1950396 A1 | 7/2008 |
| EP | 2055273 A1 | 5/2009 |
| EP | 2057969 A2 | 5/2009 |
| FR | 2574283 A1 | 6/1986 |
| FR | 2796267 A1 | 1/2001 |
| FR | 2832624 A1 | 5/2003 |
| FR | 2926212 A1 | 7/2009 |
| FR | 3043545 A1 | 5/2017 |
| GB | 806441 A | 12/1958 |
| GB | 2583537 A | 4/2020 |
| JP | 5859810 B2 | 2/2016 |
| WO | WO 1992003993 A1 | 3/1992 |
| WO | WO 1996036284 A1 | 11/1996 |
| WO | WO 1997030661 A1 | 8/1997 |
| WO | WO 2002026145 A1 | 4/2002 |
| WO | WO 2007098549 A1 | 9/2007 |
| WO | WO 2008069800 A1 | 6/2008 |
| WO | WO 2009106866 A1 | 9/2009 |
| WO | WO 2009108683 A1 | 9/2009 |
| WO | WO 2012035294 A2 | 3/2012 |
| WO | WO 2012138824 A2 | 10/2012 |
| WO | WO 2014140636 A1 | 9/2014 |
| WO | WO 2014140639 A1 | 9/2014 |
| WO | WO 2018189128 A1 | 10/2018 |
| WO | WO 2019038026 A1 | 2/2019 |
| WO | WO 2019057698 A1 | 3/2019 |
| WO | WO 2019068428 A1 | 4/2019 |

OTHER PUBLICATIONS

"Engage Modular Revision Hip System: Surgical Technique," 2007, DePuy Orthopaedics, Inc, 19 pages.
GB Search Report From GB Patent Application No. GB1905459.2, dated Oct. 1, 2019, 1 page.
PCT Search Report From PCT Application No. PCT/EP2018/070454, dated Feb. 25, 2020, 18 Pages.

* cited by examiner

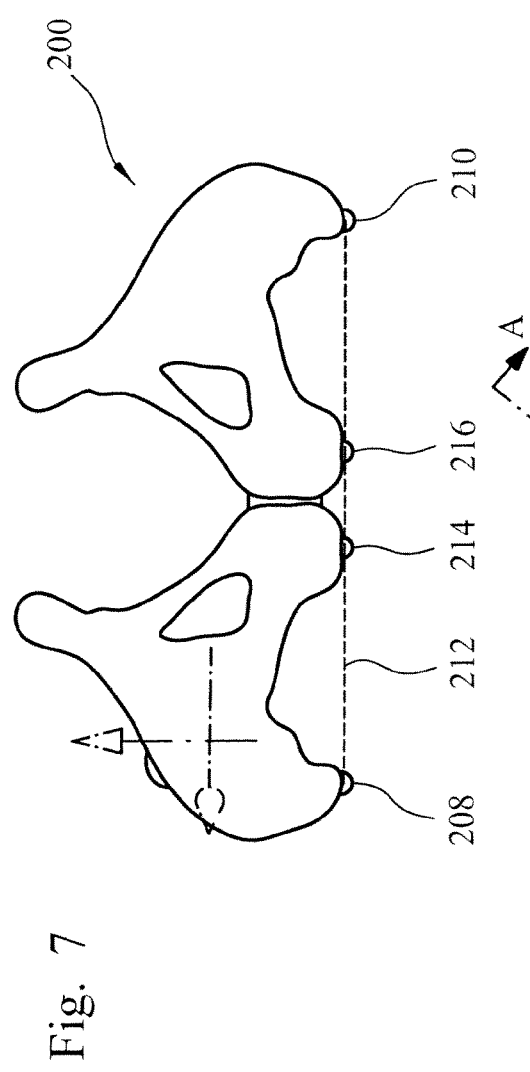
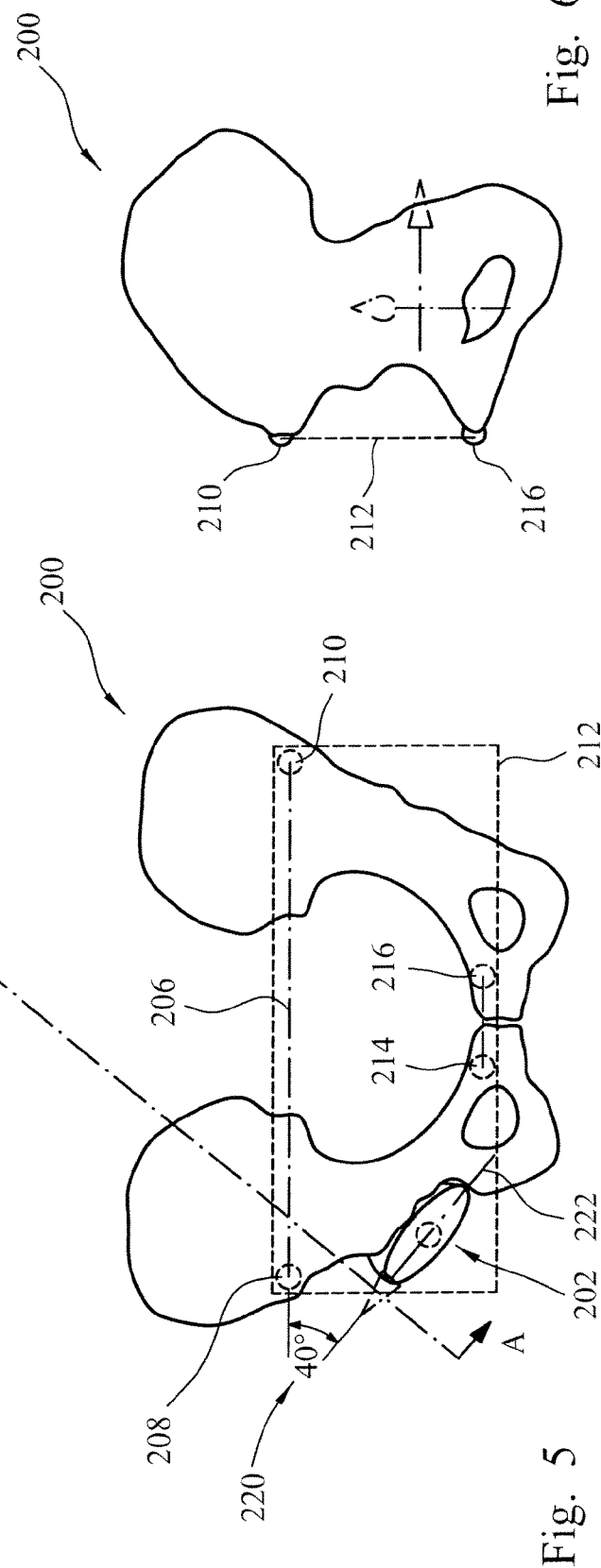
Fig. 7
Fig. 6
Fig. 5

Fig. 8
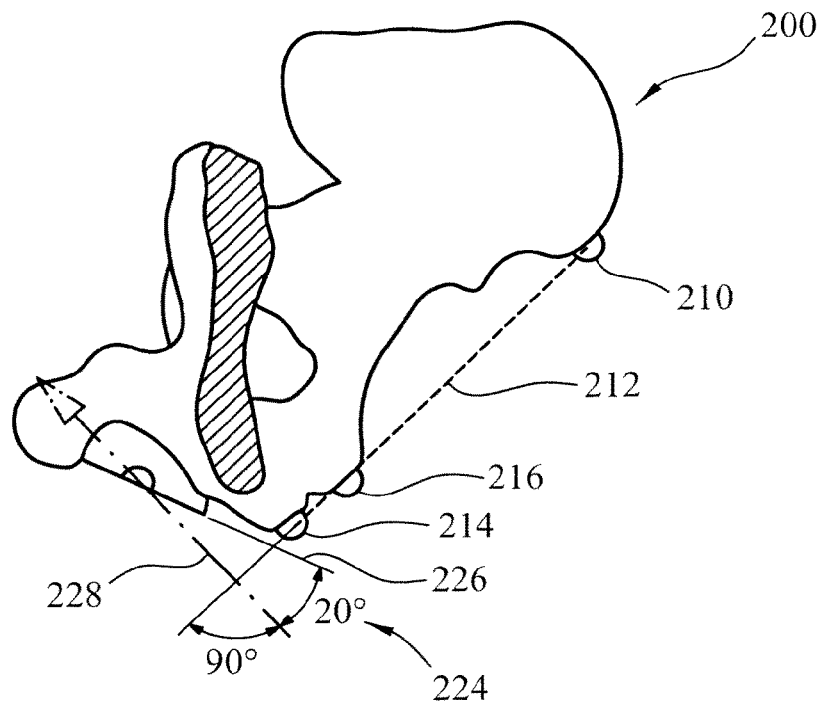
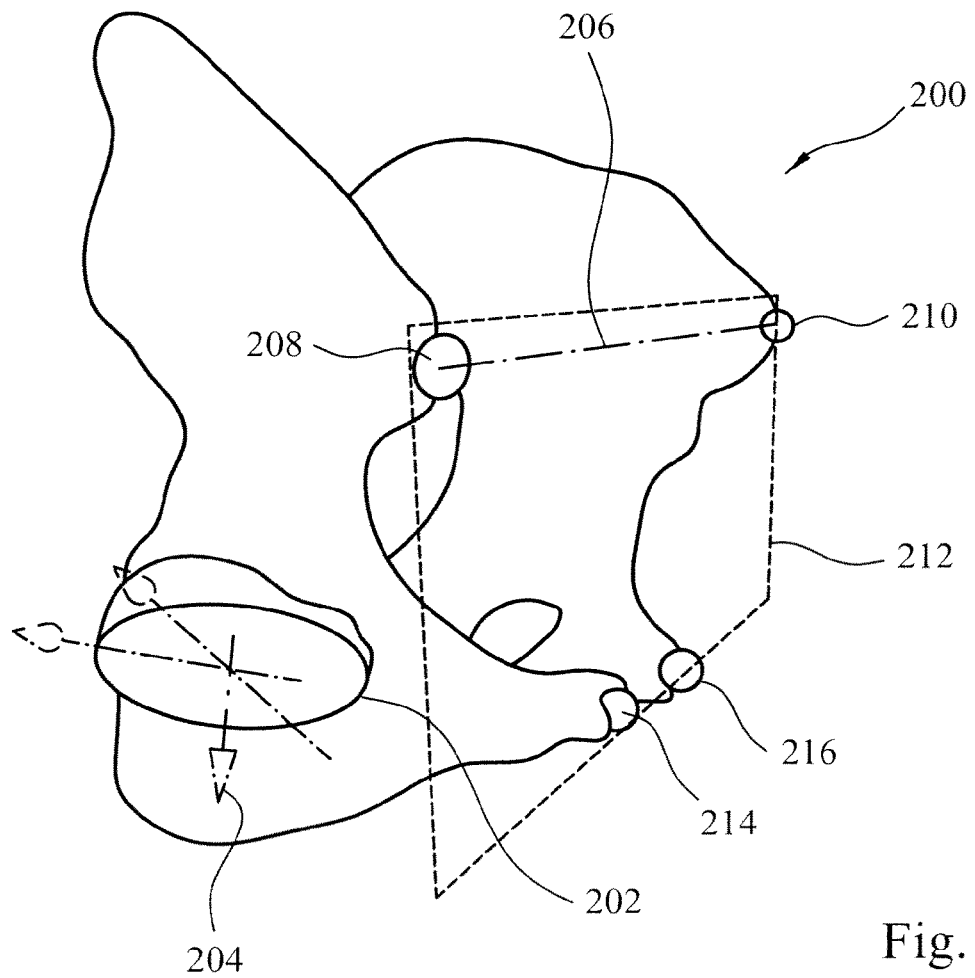
Fig. 9

FEMORAL TRIALLING KIT AND ASSEMBLY

CROSS REFERENCE TO RELATED PCT APPLICATION

This application is a National Stage 35 U.S.C. 371 of International Patent Application PCT/EP2018/059065 filed Apr. 9, 2018, which claims priority to United Kingdom Application No. 1705917.1, filed Apr. 12, 2017, all of which are incorporated by reference in their entireties.

The present invention relates to hip surgery and in particular to trial parts which may be used during trialling of a hip joint and methods of use of such trial parts.

A variety of methods of hip surgery are generally known. The hip joint may generally be considered a ball and socket joint in which the head of the femur articulates within the acetabular cavity of the pelvis. Some methods of hip surgery may involve the replacement of one or more parts of the hip joint with one or more prosthetic components. This may be to replace damaged, worn, diseased or otherwise imperfect parts of the hip joint including the respective articulating surfaces of the acetabular cavity and/or femoral head.

Different surgical procedures may involve replacement of a part of the acetabulum or the femoral head or both. Some procedures, sometimes referred to as resurfacing procedures, may involve replacement of only the articulating surface of the femoral head. Other procedures may involve replacement of the entire femoral head. Such procedures often also use a femoral or stem component which is implanted in the resected femur and having a neck to which the femoral head is attached. In some procedures, a prosthetic cup may be implanted in a prepared acetabular cavity to provide a cavity in which the femoral head or prosthetic femoral head may articulate when the joint is reduced. Surgical procedures in which both the acetabulum and at least a part of the femoral head are replaced with prosthetic components are generally referred to as total hip replacement procedures.

During hip surgery procedures, some surgeons may sometimes use one or more trial components, which have the same geometry and size as the intended prosthetic components, so that the surgeon may trial the joint before final implantation of one or both of the prosthetic components. For example, the surgeon may use trial components to check that the size, position or orientation of one or more of the components is suitable. Other surgeons may opt not to use trial components or may use them occasionally based on their professional judgement.

One of the considerations in hip surgery is the angular orientation of the acetabular cavity. When the acetabulum is replaced with an acetabular cup, then it is often an aim of the surgeon to place the acetabular cup so that it is pointing generally in a preferred direction or range of directions. The orientation of an acetabular cup is often defined in terms of an angle of abduction, or inclination, and an angle of anteversion.

A variety of approaches have been used to try and assess the angular orientation of an acetabular cup, either a trial or a prosthesis, after placement in the acetabular cavity.

Anatomical approaches may be used in which the surgeon uses either their experience and/or a piece of instrumentation, in order to gauge, by inspection or instrumentation, the angular orientation of the acetabular cup relative to one or more anatomical features of the patient's pelvis. However, there is often limited access to the surgical site, particularly for minimally invasive approaches, and therefore this is often not easy nor accurate.

Other approaches may use markings or other features on the trial or prosthetic components in order to gauge the angular orientation of the acetabular cup relative to the patient's pelvis.

For example "The Ranawat Sign A Specific Maneuver to Assess Component Positioning in Total Hip Arthroplasty", Lucas, David H., and Scott, Richard D., Journal of Orthopaedic Techniques, Vol. 2, No. 2, June 1994, describes a method of intraoperative assessment of component orientation for total hip arthroplasty. With the patient in the true lateral decubitus position, the femur is internally rotated without hip flexion until a flat underside of the prosthetic head (generally perpendicular to the femoral neck) is coplanar with a rim of the acetabular cup. The amount of internal rotation necessary to achieve this position is known as the Ranawat sign and relates to the combined anteversion of the acetabular and femoral components of the joint. For example a Ranawat sign of 45° may correspond to a cup anteversion of 30° and a femoral anteversion of 15°. However, any knee laxity or deformity can influence the interpretation of this value. Also, there may be difficulty in assessing the actual magnitude of the angle of internal rotation. Further, different surgeons may have different approaches to manipulating the patient's leg and also any one surgeon's approach may not easily be reproducible from patient-to-patient either by that same surgeon or by other surgeons.

WO 2009/108683 describes another approach in which markings are applied to a femoral head and in which the surgeon again applies an amount of internal rotation to the patient's leg, during trial reduction, so that the angle between the rim of the acetabular cup and various markings on the femoral head indicates the angular position of the acetabular cup relative to the patient's pelvis. A leg position is used in which the patient's leg is in full, relaxed extension at zero degrees abduction, zero degrees anteversion and approximately 15° internal rotation, or otherwise internally rotated by an amount equal to the amount of version of the natural or artificial femoral neck. Hence, this approach also requires the surgeon to apply a specific amount of internal rotation to the patient's leg. Again, it may be difficult to apply the correct amount of internal rotation, there may be inaccuracies introduced by deformities of the patient's leg and the surgical technique may be difficult to reproduce and/or reliably learn. This is particularly the case for a relatively small angle, 15°, as even a relatively small error in the amount of internal rotation, for example 5°, is a large proportion (33%) of the target internal rotation.

Other approaches and associated instrumentation are described in US 2005/0107799. An accessory for implanting a hip cup, includes a manipulable cup, a manipulation head having a hemispherical portion and a circular rim around it for aligning the manipulable cup in the acetabulum. A device for immobilizing the aligned position of the manipulable cup is provided and allows a guide to be set for alignment of a bone bur and a drive-in instrument for reaming placing the acetabular cavity and placing the cup. In another approach, a manipulable cup is located in the acetabulum and its orientation can be adjusted by a handle until a lip of the manipulable cup is parallel with an equatorial line on a femoral head or a plane on the reverse of a femoral head Hence, apparatus and/or methods making accurate intraoperative assessment of acetabular cup placement simpler, easier and/or more reliable would be beneficial.

A first aspect of the invention provides a femoral trialling kit for assessing acetabular cup orientation during a left hip joint surgical procedure and a right hip joint surgical procedure, comprising: a trial femoral head having an inner wall defining a cavity extending along a head axis and a visual alignment guide on an outer surface of the trial femoral head; and a trial femoral neck having a taper at a free end, the tapering being receivable within the cavity, wherein one of the taper and the inner wall has a first anti-rotation feature and a second anti-rotation feature, the first anti-rotation feature and the second anti-rotation feature being inclined, and the other of the taper and the inner wall has a third anti-rotation feature, and wherein the trial femoral head is attachable to the trial femoral neck in a first angular configuration corresponding to a right hip joint, in which the third anti-rotation feature and the first anti-rotation feature engage, and a second angular configuration corresponding to a left hip joint, wherein the third anti-rotation feature and the second anti-rotation feature engage.

The visual alignment guide may comprise a single indicium only. The visual alignment guide may be a single line or band.

The visual alignment guide may be tilted relative to the head axis. The visual alignment guide may define a plane and the plane and the head axis may subtend and acute angle in the range of approximately 20° to 40°. The acute angle may be approximately 31°.

The single indicium may be in the form of a band having a first colour. The surface of the trial head may have a second colour. The first colour and the second colour may be different colours. The first colour may be a darker colour than the second colour.

The single indicium may have a width of at least 3 mm. The single indicium may have a width in the range of 3 mm to 5 mm. Preferred values of the width of the single indicium include 3.5 mm and 4 mm.

The trial femoral neck may include a neck indicium. The neck indicium may act as an angular position datum. The trial femoral head may include a first head indicium and/or a second head indicium on the outer surface of the trial femoral head. The first head indicium and the second head indicium may be positioned about the head axis so that when the trial femoral head is attached to the trial femoral neck in the first angular configuration the first head indicium is aligned with the neck indicium and/or when the trial femoral head is attached to the trial femoral neck in the second angular configuration the second head indicium is aligned with the neck indicium. The neck indicium may be or include a line. The first head indicium may be a right indicium and/or may be or include an R and/or a dash. The second head indicium may be a left indicium and/or may be or include an L and/or a dash.

The neck indicium may be on a superior and/or lateral surface of the trial femoral neck.

The trial femoral neck may include a first neck indicium and a second neck indicium on opposed sides of the trial femoral neck. The trial femoral head may include a first head indicium and a second head indicium on the outer surface of the trial femoral head. The first head indicium and the second head indicium may be respectively positioned about the head axis so that when the trial femoral head is attached to the trial femoral neck in the first angular configuration the second head indicium is aligned with the second neck indicium and when the trial femoral head is attached to the trial femoral neck in the second angular configuration the first head indicium is aligned with the first neck indicium.

The first neck indicium and the second neck indicium may be visually distinguishable. The first head indicium and the second head indicium may be visually distinguishable. The first neck indicium and the first head indicium may be visually related, similar or the same. The second neck indicium and the second head indicium may be visually related, similar or the same.

The first neck indicium, the second neck indicium, the first head indicium and the second head indicium may be all the same shape. For example, they may all be triangular.

The first neck indicium and the first head indicium may be the same first colour. The second neck indicium and the second head indicium may be the same second colour. The first colour and the second colour may be different colours. The first colour may be white and the second colour may be black.

One of the taper and the inner wall may have a fourth anti-rotation feature. The fourth anti-rotation feature may be inclined to the first anti-rotation feature and the second anti-rotation feature. The other of the taper and the inner wall may have a fifth anti-rotation feature. The fifth anti-rotation feature may be inclined to the third anti-rotation feature. In the first angular configuration corresponding to the right hip joint, the fifth anti-rotation feature and the fourth anti-rotation feature may engage. In the second angular configuration corresponding to the left hip joint, the first anti-rotation feature and the fifth anti-rotation feature may engage.

The taper may have a free end and an outer portion. The or each anti-rotation feature may be provided at the free end of the taper. The outer portion of the taper may have a circular cylindrical form. The inner wall defining the cavity may have an outer portion and an inner portion. The inner portion may provide the or each anti-rotation feature. The outer portion may have a circular cylindrical form.

The femoral trialling kit may further include a retention mechanism arranged to releasably attach the trial femoral head to the taper.

The retention mechanism may be configured to provide a friction fit between the taper and the cavity. The retention mechanism may include an O-ring. The O-ring may be made from a compliant material, such as a rubber, silicone or similar. The O-ring may be provided around the taper, and may be located in a groove extending around the taper.

The retention mechanism may include a clip. The clip may be arranged to interact between the taper and the cavity. The clip may be in the form of a C-clip or C-ring. The C-clip may be provided in a groove extending around the tape and a corresponding groove may be provided in a wall defining the cavity of the trial femoral head. The c-clip or c-ring may be made of a metal, such as stainless steel.

The or each anti-rotation feature may be a surface. The surface may be a flat surface or a curved surface or an irregular shaped surface. The or each surface on the taper and the or each surface within the cavity may be configured so that surfaces on the taper will mate or engage or abut with surfaces within the cavity. Matching pairs of surfaces may provide better anti-rotation control.

The anti-rotation features may be male and/or female features. The or each anti-rotation feature of the taper may be a male feature and the or each anti-rotation feature of the cavity may be a female feature. The or each anti-rotation feature of the cavity may be a male feature and the or each anti-rotation feature of the taper may be a female feature.

The trial femoral head may include a first grip feature and/or a second grip feature in the outer surface. The first and/or second grip features may be provided on the same side of the trial femoral head.

The first grip feature and/or the second grip feature may be in the form of a recess. The or each recess may be adapted or configured to receive finger tips of a user in use.

The visual alignment guide may be positioned on the outer surface of the trial femoral head to correspond to an inclination angle of less than 45° of an acetabular cup in a pelvis of a patient, when the trial femoral head is mounted on the trial neck on a stem component within a femur of the patient with the trial hip joint reduced and in a neutral position. The visual alignment guide may be positioned on the outer surface of the trial femoral head to correspond to an inclination angle of an acetabular cup between approximately 20° and approximately 40°. The visual alignment guide may be positioned on the outer surface of the trial femoral head to correspond to an inclination angle of an acetabular cup of approximately 40°. The visual alignment guide may be positioned on the outer surface of the trial femoral head to correspond to an anteversion angle of the acetabular cup of between approximately 10° and approximately 20°. The visual alignment guide may be positioned on the outer surface of the trial femoral head to correspond to an anteversion angle of the acetabular cup of approximately 20°.

The anti-rotation features may be configured such that the trial femoral head is rotated by less than 180° in the first configuration compared to the second configuration. The anti-rotation features may be configured such that the trial femoral head is rotated by less than 150° in the first configuration compared to the second configuration. The anti-rotation features may be configured such that the trial femoral head is rotated by approximately 144° in the first configuration compared to the second configuration.

The femoral trialling kit may further comprise a femoral component to which a base of the trial femoral neck is releasably attachable. A neck angle when the trial femoral neck is attached to the femoral component may be greater than or less than 135°. The femoral component may be a stem, a broach or a rasp or similar.

A second aspect of the invention provides a femoral trialling assembly comprising an assembly of the femoral trialling kit of the first aspect of the invention, including any preferred features thereof.

A third aspect of the invention provides a method of assembling a trial femoral assembly comprising a trial femoral head having an inner wall defining a cavity and a trial femoral neck having a taper being receivable within the cavity, the method comprising:

determining whether the assembly is to be used to trial a left hip or a right hip; and attaching the trial femoral head to the trial femoral neck in a first angular configuration corresponding to a right hip joint or attaching the trial femoral head to the trial femoral neck in a second angular configuration corresponding to a left hip joint.

One of the taper and the inner wall may have a first anti-rotation feature and a second anti-rotation feature, the first anti-rotation feature and the second anti-rotation feature being inclined, and the other of the taper and the inner wall may have a third anti-rotation feature.

The third anti-rotation feature and the first anti-rotation feature may engage in the first angular configuration.

The third anti-rotation feature and the second anti-rotation feature may engage in the second angular configuration.

The method may further comprise disengaging the trial femoral head from the trial femoral neck; rotating the trial femoral head by an angle greater than or less than 180° about a neck axis of the trial femoral neck; and re-attaching the trial femoral head to the trial femoral neck in the other of the first angular configuration and the second angular configuration.

An embodiment of the invention will now be described in detail, by way of example only, and with reference to the accompanying drawings, in which:

FIG. 5 shows a coronal view of a pelvis;

FIG. 6 shows a sagittal view of the pelvis of FIG. 5;

FIG. 7 shows a transverse view of the pelvis of FIGS. 5 and 6;

FIG. 8 shows a partial cross sectional perspective view of the pelvis along line A-A of FIG. 5;

FIG. 9 shows a perspective view of the pelvis;

Similar items in different Figure shared common reference signs unless indicated otherwise.

Before describing the apparatus and/or methods of the invention, the geometry of a hip joint will be discussed generally. In the below, a right hip joint is described, but it will be appreciated that a similar discussion applies to a left hip joint. Also, the following discussion is intended to relate to both the pre-operative natural, or native, hip joint, as well as to the artificial, or prosthetic, hip joint. Hence, although the magnitude of the various angles may vary between the native hip joint and the prosthetic hip joint, the definitions of those angles may be generally the same for the native and prosthetic hip and may be determined by the positions and/or orientations of the various parts making up the native hip joint and prosthetic hip joint respectively.

Figure 1:
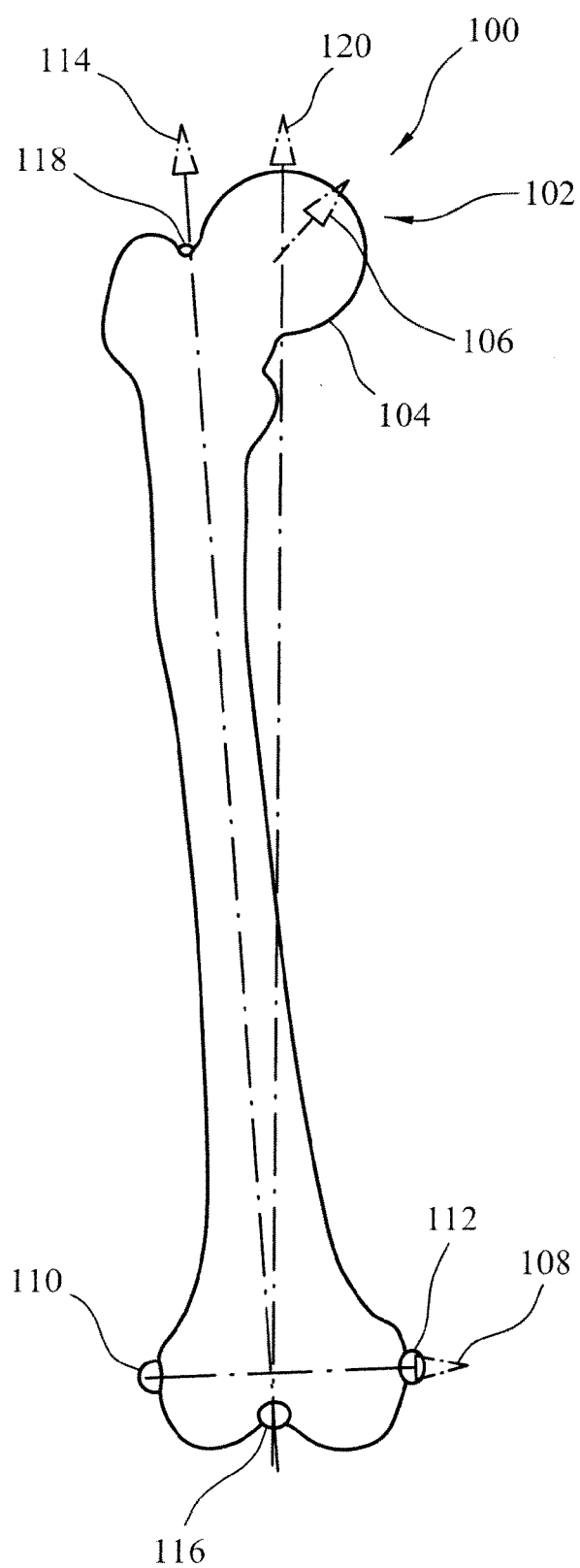
FIG. 1 shows a coronal view of a femur.
Figure 2:
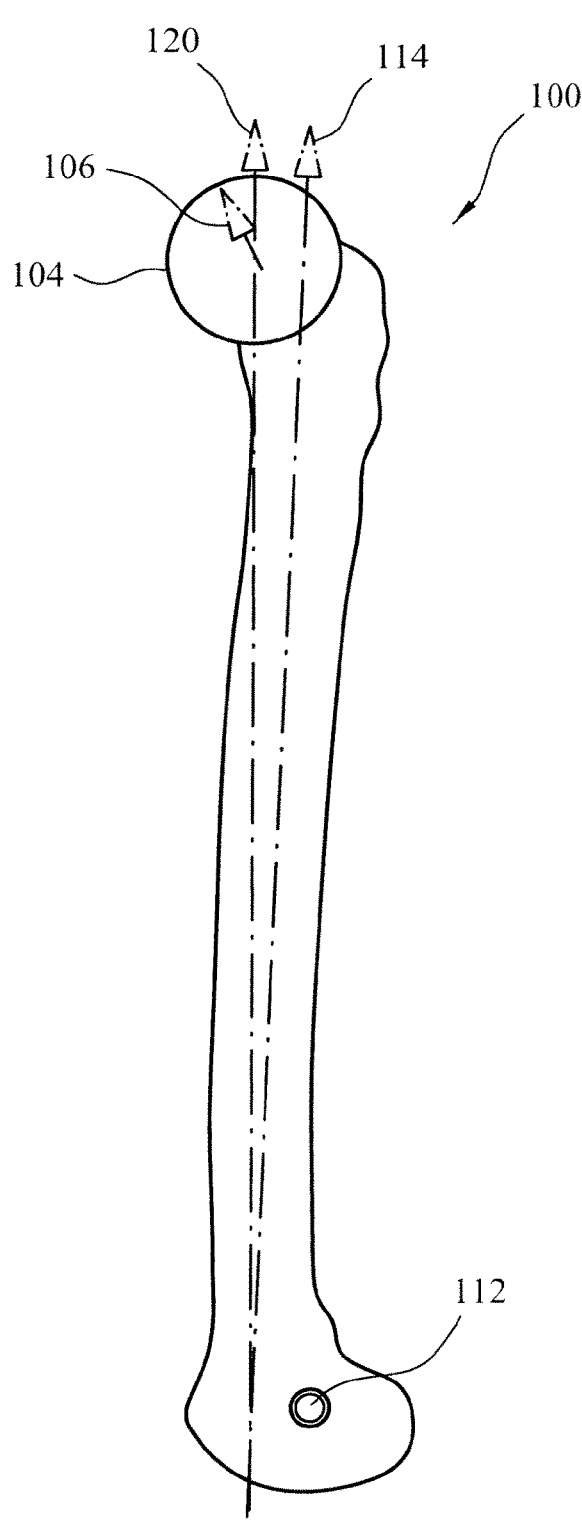
FIG. 2 shows a sagittal view of the femur of FIG. 1.
Figures 3, 4:
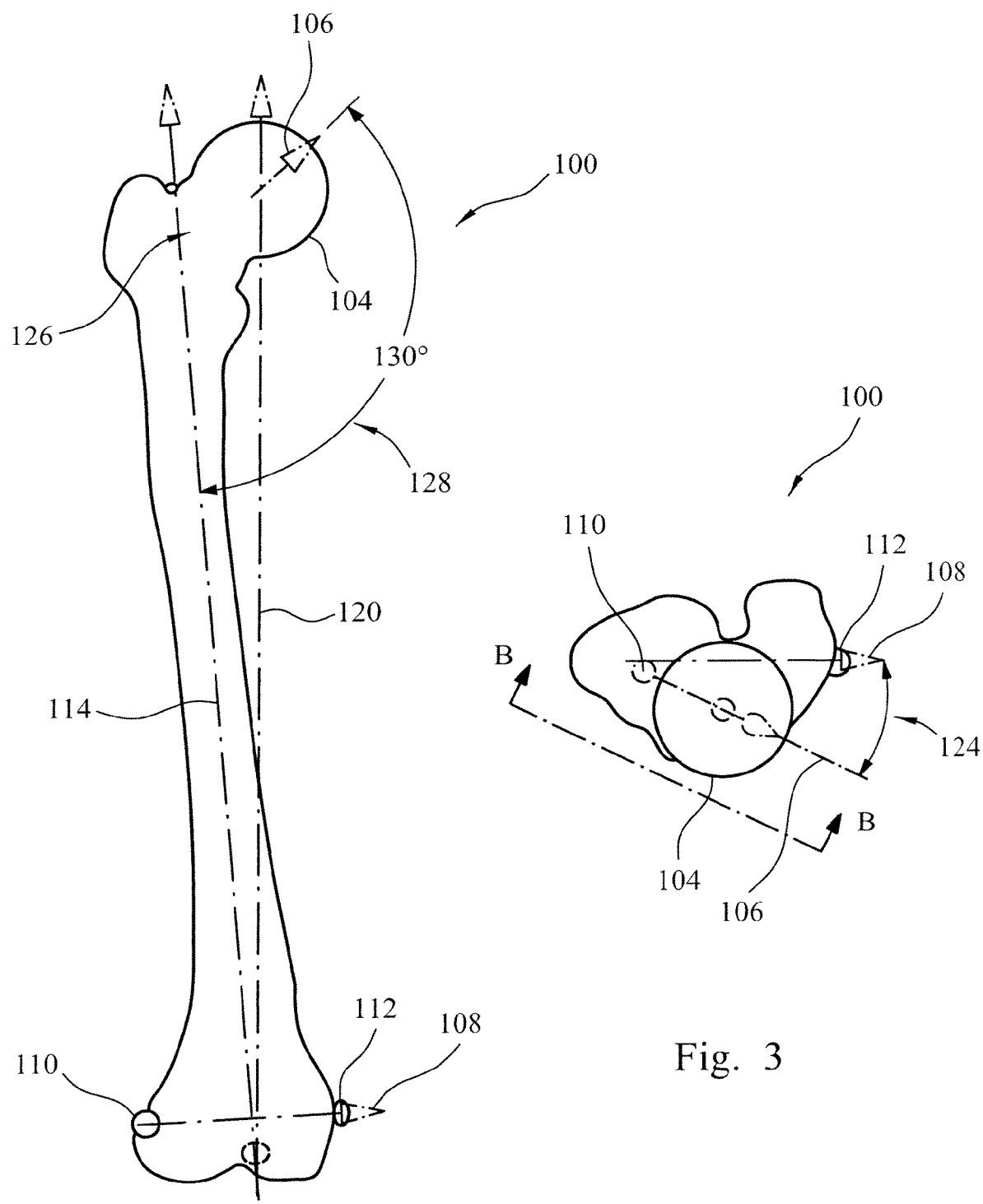
FIG. 3 shows a transverse view of the femur of FIGS. 1 and 2.
FIG. 4 shows a view of the femur in a plane parallel to the anatomic axis and the neck of the femur.

With reference to FIGS. 1 to 4, there are shown various different views of a right femur 100. In particular FIG. 1 shows a coronal view in the anterior to the posterior direction (generally herein the AP direction), FIG. 2 shows a sagittal view in the medial to the lateral direction (generally herein the ML direction), FIG. 3 shows a transverse view in the superior to the inferior direction, and FIG. 4 shows a view of the femur in a plane parallel to the anatomic axis of the femur and the neck of the femur as explained in greater detail below. Pre-operatively, the proximal part of the femur 100 includes the native femoral neck and native femoral head. Intra-operatively and post-operatively the proximal part of the femur may include various trial or prosthetic parts or components providing trial or prosthetic femoral necks and femoral heads. The following will refer generally to femoral necks and femoral heads and is intended to include native, trial or prosthetic ones.

With particular reference to FIGS. 1 and 2, the proximal part 102 of femur 100 includes a femoral head 104 (represented by a sphere) attached to a femoral neck 126, best illustrated in FIG. 4, having a neck axis extending generally in the direction of arrow 106. The femur 100 has an epicondylar axis 108 extending between the lateral femoral epicondyle 110 and the medial femoral epicondyle 112. The femur 100 also has an anatomic axis 114 extending between, for example, the distal femur intercondylar notch 116 and the piriformis fossa, close to the medial face of the greater trochanter. The femur 100 also has a mechanical axis 120 extending between, for example, close to the distal femur intercondylar notch 116 and the centre of the femoral head 104. The anatomical axis 114 and mechanical axis 120 of the femur 100 may be defined by other anatomical points in other embodiments.

With reference to FIG. 3, a femoral neck anteversion angle 124 can be defined as the angle in the transverse plane subtended by the femoral neck axis 106 and the epicondylar axis 108. In practice, the femoral neck anteversion angle for the native neck is typically in the range of about 12° to 15°, but may have other values. Neck anteversion angle 124 is a measure of the anteversion of the femoral neck relative to the local anatomy of the femur 100.

FIG. 4 shows a view of the femur 100 in a plane parallel to line BB of FIG. 3, which is parallel to the femoral neck axis 106, and the anatomical axis 114, and which more clearly shows the femoral neck 126. FIG. 4 also illustrates the neck angle 128 subtended between the femoral neck axis 106 and the anatomical axis 114 of the femur. The native neck angle 128 varies from patient to patient, but is typically about 130°. The neck angle 128 for a trial or prosthetic implant is usually fixed by the implant design, unless the implant is adjustable, and is often intended to approximately reproduce the native geometry and so may also be about 130°. In the following a neck angle 128 of 130° may be used as an example, but it will be appreciated that in other embodiments, other neck angle values may also be used.

Hence during hip surgery in which a prosthetic femoral component is used, one of the variables is the femoral neck anteversion angle 124, which generally measures how far forward the femoral neck 126 is directed compared to the medial-lateral axis of the femur.

With reference to FIGS. 5 to 9, there are shown various different views of a pelvis 200 and right acetabulum. In particular FIG. 5 shows a coronal view in the anterior to the posterior direction (generally herein the AP direction), FIG. 6 shows a sagittal view in the medial to the lateral direction (generally herein the ML direction), FIG. 7 shows a transverse view in the superior to the inferior direction, FIG. 8 shows a partial sectional view along line A-A of FIG. 5, and FIG. 9 shows a perspective view of the pelvis 200 with the anterior pelvic plane (APP) vertical and the transverse axis generally horizontal. Pre-operatively, the pelvis 200 includes an acetabulum which provides a native socket in which the native femoral head is received and articulates. Intra-operatively and/or post-operatively the pelvis may include various trial or prosthetic implants, such as trial or prosthetic acetabular cups (with or without liners depending on the specific implant system being used). The following will refer generally to the acetabulum or acetabular cup and is intended to include the native acetabulum as well as trial or prosthetic components.

As illustrated in FIG. 5, the acetabulum 202 may be represented by a hemisphere or hemispherical cup which generally has a position and an orientation. The orientation or direction of the acetabulum may generally be defined by two angles. A first angle indicates how much the acetabulum is directed forward or backward (generally referred to as anteversion when pointing anteriorly and retroversion when pointed posteriorly) relative to the pelvis. A second angle indicates how much the acetabulum is pointing downward or in an inferior direction (generally referred to as inclination or abduction) relative to the pelvis. The direction of the acetabulum may be defined by an acetabular axis 204, best illustrated in FIG. 9, which generally passes through the centre of the mouth of the acetabulum and perpendicular to the plane of the mouth of the acetabulum.

The pelvis 200 includes a transverse axis 206 passing between the right ASIS 208 and the left ASIS 210. An anterior pelvic plane 212 (generally referred to as APP in the following) is defined by the transverse axis 206 and first and second points on the symphysis pubis 214, 216.

As best illustrated in FIG. 5, an inclination angle for the acetabulum or acetabular cup 202 may be defined by the angle 220 subtended by the transverse axis 206 and a long axis, or inclination axis, 222 of the acetabular cup 202 within, or parallel to, the anterior pelvic plane 212. In FIG. 5, the illustrated inclination angle 220 is approximately 40°. FIG. 8 shows a view of a cross section of the pelvis 200 along line A-A in FIG. 5 and in a direction along the long axis 222 of the acetabular cup 202. Hence, FIG. 8 shows the plane generally perpendicular to the long axis 222 of the pelvic cup 202. From FIG. 8, an anteversion angle 224 may be defined as the angle subtended between the plane 226 of the mouth of the acetabular cup and a plane 228 perpendicular to the anterior acetabular plane 212. Hence, as illustrated in FIG. 8, the acetabulum or acetabular cup 202 has an anteversion angle 224 of approximately 20°.

Hence, as illustrated in the perspective view of the pelvis 200 in FIG. 9, the acetabulum or acetabular cup 202 has an orientation corresponding to an inclination of 40° and an anteversion of 20°. These angles may be referred to as radiographic angles as they are based on the APP view of the pelvis illustrated in FIG. 5 and which is the view of the pelvis typically radiographically imaged or X-rayed and which images are often used by surgeons pre-, intra- and/or post operatively to assess acetabular orientation.

Figure 10:
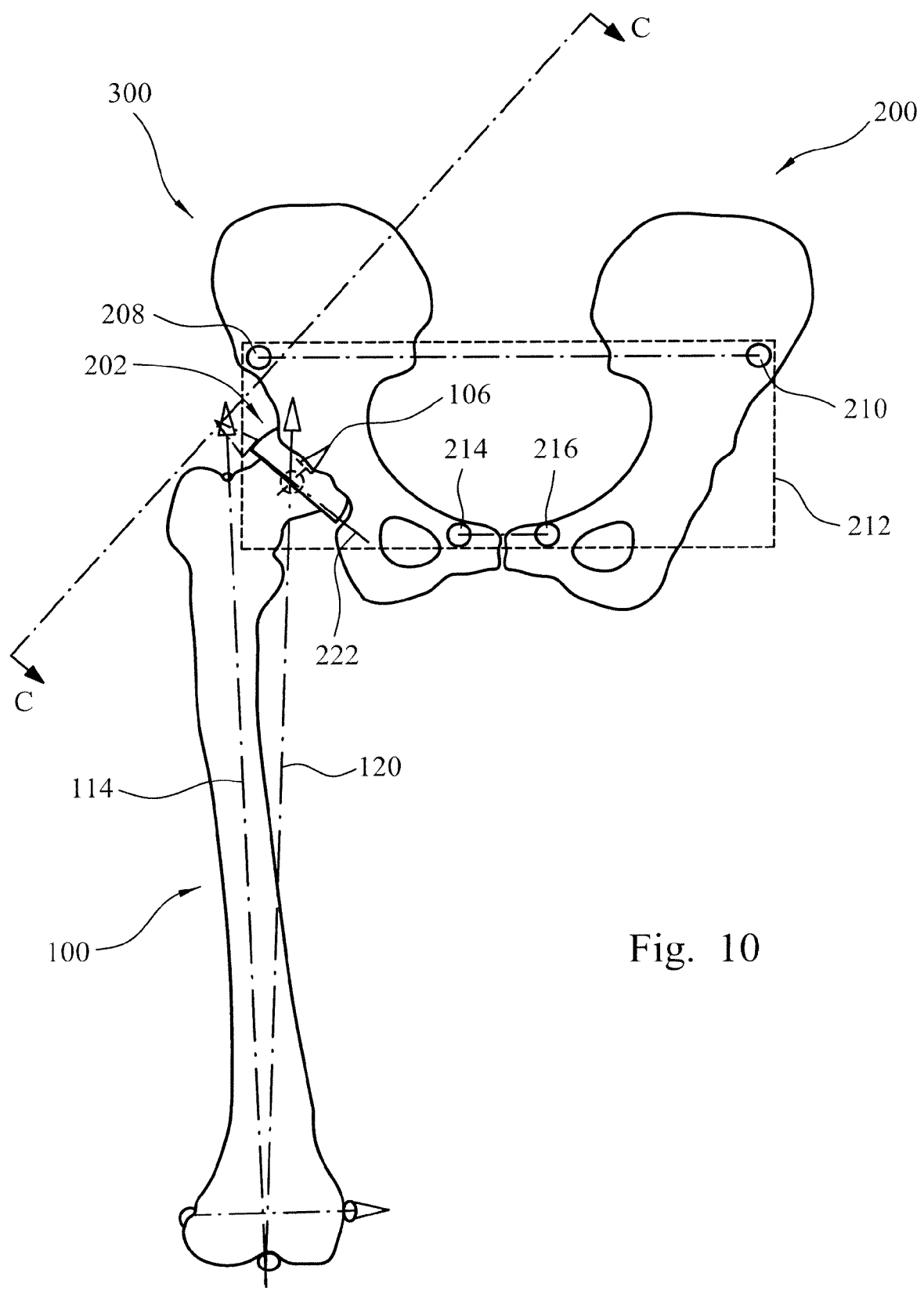
FIG. 10 shows a coronal view of a hip comprising the femur of FIGS. 1 to 4 and the pelvis of FIGS. 5 to 9.
Figure 11:
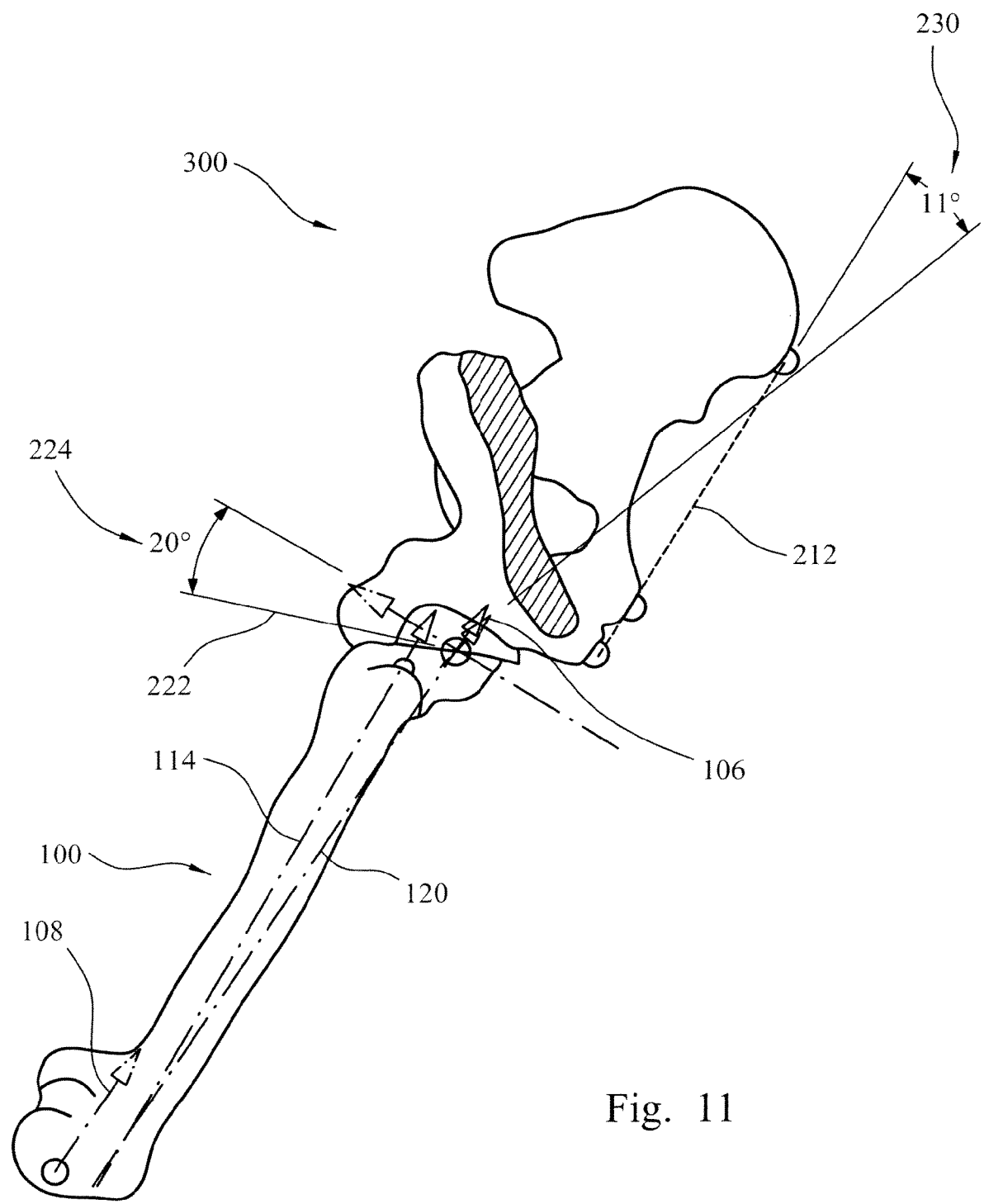
FIG. 11 shows a partial cross sectional perspective view of the pelvis along line C-C of FIG. 10.

With reference to FIGS. 10 to 11, there are shown various different views of a right hip joint 300 formed by femur 100 and pelvis 200. In particular, FIG. 10 shows a coronal view in the anterior to the posterior direction (generally herein the AP direction), similar to FIGS. 1 and 5 combined. In FIG. 10, the femur has been placed in a neutral position as described in greater detail below. FIG. 11 shows a partial section along line C-C of FIG. 10 and viewed in a direction along the inclination axis 222 of the acetabular cup 202. Hence, the plane of FIG. 11 is generally perpendicular to the direction of the inclination axis 222 of the acetabular cup.

As illustrated in FIG. 11, the acetabular cup 202 has an anteversion angle 224 of 20° in the plane perpendicular to the inclination axis 222 of the acetabulum. FIG. 11 also illustrates the femoral anteversion angle 230 in the plane perpendicular to the inclination axis of the acetabulum and being defined by the angle 230 subtended in that plane by the femoral neck axis 106 and the anterior pelvic plane 212. As illustrated in FIG. 11, the apparent femoral anteversion angle 230 is approximately 11°.

Hence, as can be seen the overall geometry of the hip joint arises from the orientation of the acetabulum relative to the pelvis and also the orientation of the femoral neck relative to the femur. In the illustrated example, the overall or combined anteversion of the hip joint 200 shown in FIGS. 10 and 11 is the combination of the acetabular anteversion, about 20°, and the amount of femoral anteversion projected into the same plane, which in this example is approximately 11°. Hence, the combined anteversion of the hip joint 300 in this plane is about 31°.

However, in practice, when surgeons talk about a combined anteversion of about 35°, this may be arrived at by adding absolute values of angles in different planes, 15° anteversion of the neck relative to the femur in a first plane and 20° anteversion of the acetabulum relative to the pelvis in a second, different plane, to give approximately 35°. In practice, the combined anteversion is assumed to be in the range of approximately 30° to 40°, as being typically greater than 30° and less than 40°, and that any measurement or assessment is likely to be accurate to plus or minus a few degrees anyway and so measurement of the angles in different, non-parallel planes is not crucial.

Herein, combined anteversion may refer, depending on the context, to the general idea that the anteversion of a hip joint is the combined effect of the degree of anteversion of the femoral neck relative to the femur and also the degree of anteversion of the acetabulum relative to the pelvis. More specifically, for non-extreme cases, combined anteversion may also refer to a general rule of thumb that the sum of the acetabular anteversion and the femoral anteversion, measured in the same plane, should have a certain value, for example approximately 35°. Hence, if a low value of one occurs, then the other can be increased (or vice versa) in order to bring the combined anteversion closer to this target value.

Figure 12:
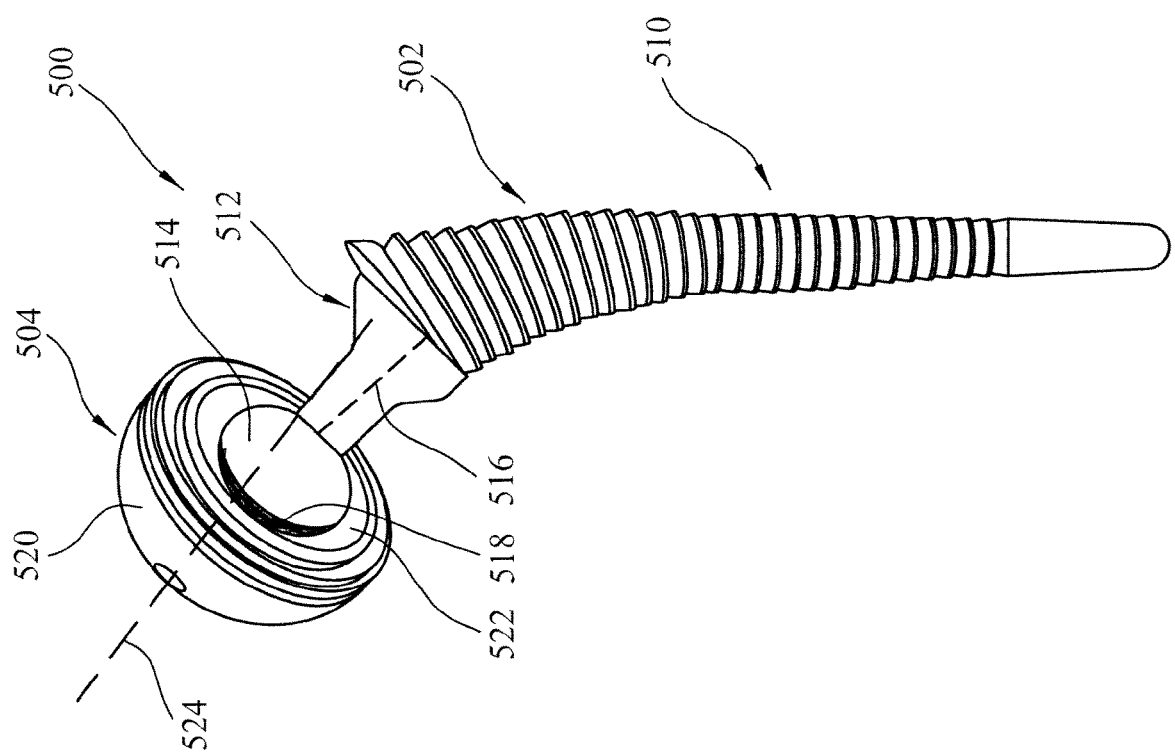
FIG. 12 shows a view of right and left hip trialling assemblies having a first geometry.
Figure 12:
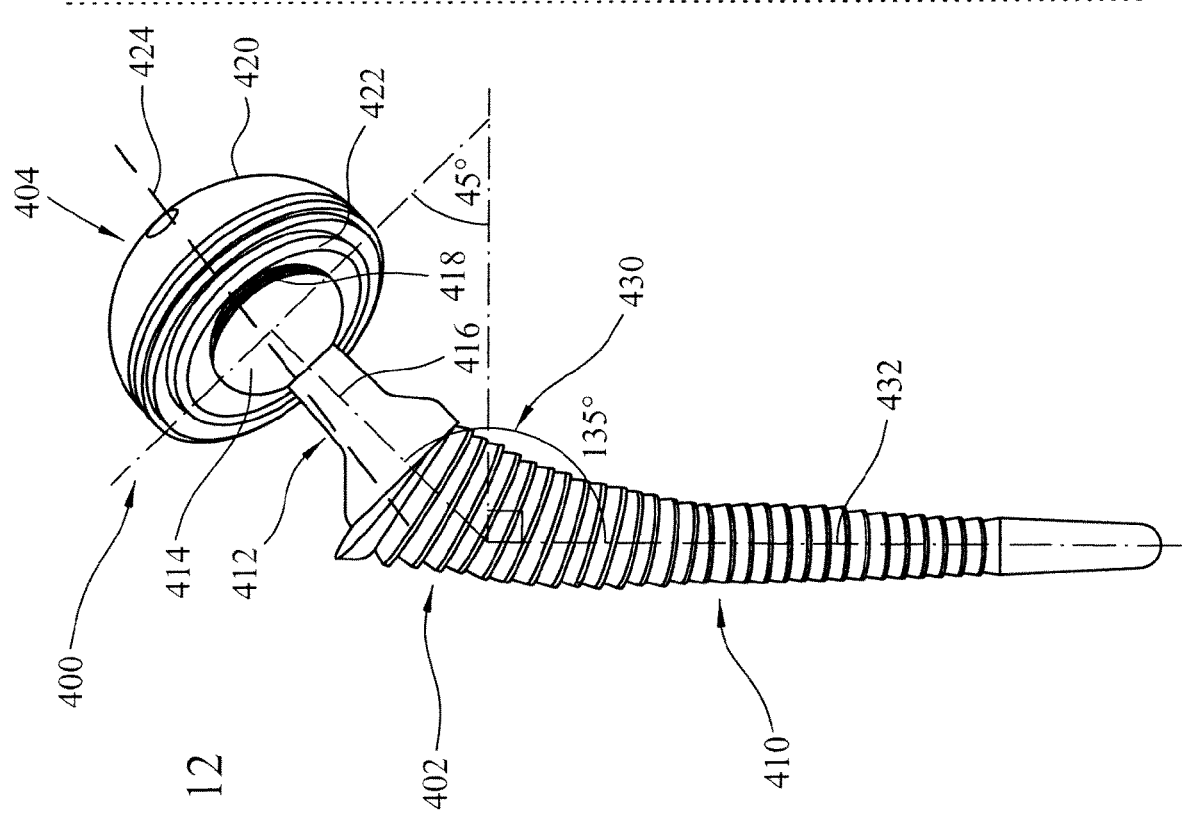

With reference to FIG. 12 there is shown a view of a first trial hip joint 400 and a second trial hip joint 500. The first trial hip joint 400 is for a right hip joint and the second trial hip joint 500 is for a left hip joint. The first trial hip joint 400 includes a femoral part 402 and an acetabular part 404. The femoral part includes a stem component 410, in the form of a reamer or broach, a trial neck 412, which is releasably attached to a superior part of the reamer, and a trial femoral head 414, which is releasably attached to the trial neck 412. The acetabular part 404 includes an acetabular cup 420 and optionally an acetabular liner 422. The acetabular cup 420 is generally hemispherical and defines a hemispherical cavity in which the acetabular liner 422 may be received and which itself defines a generally hemispherical cavity in which the trial femoral head 414 can be received and will articulate.

Similarly, the second trial hip joint 500 includes a femoral part 502 and an acetabular part 504. The femoral part includes a stem component 510, in the form of a reamer or broach, a trial neck 512, which is releasably attached to a superior part of the reamer, and a trial femoral head 514, which is releasably attached to the trial neck 512. The parts of the first trial hip joint 400 and second trial hip joint 500 may be the same parts.

The acetabular part 504 includes an acetabular cup 520 and an acetabular liner 522. The acetabular cup 520 is generally hemispherical and defines a hemispherical cavity in which the acetabular liner 522 is received and which itself defines a generally hemispherical cavity in which the trial femoral head 514 can be received and will articulate.

FIG. 12 shows a view of the first and second trial hip joints in a plane parallel to the plane of the main body of the stem component 410, 510 and in which a neck axis 416, 516 of the trial neck lies. In use, the stem component will be located within a cavity within a femur of a patient and the stem component will have an angle of version, typically anteversion, relative to the femur as discussed above.

The acetabular components 404, 504 have an orientation relative to a pelvis of the patient which can be defined by an anteversion angle and an inclination or abduction angle as discussed above. The anteversion angle is generally the angle by which the cup is rotated in the anterior direction relative to the coronal plane of the patient's pelvis and the inclination angle is generally the angle by which the cup is rotated in an inferior direction relative to the transverse plane of the patient's pelvis. The direction of each acetabular cup can be defined by a respective acetabular cup axis 424, 524 which passes through the pole of the cup and perpendicular to the plane of the mouth of the cup, and through the centre of the generally circular mouth of the cup. Hence, the acetabular cup orientation relative to the pelvis can be defined by the angles of anteversion and inclination of the acetabular cup axis.

The trial femoral head 414, 514 is generally spherical and includes a trial cavity extending along a femoral head axis of the trial femoral head passing through the pole of the trial femoral head and which is coincident with the neck axis 416, 516. The trial cavity provides a socket into which a free end of the trial neck can be received as a spigot to provide a releasable attachment mechanism for releasably attaching the trial femoral head 414, 514 to the trial neck 412, 512. The trial femoral head also includes at least one indicium in the form of a band of colour 418, 518 on the surface of the trial femoral head, and which is black in FIG. 1, and which extends around a great circle or equator of the trial head, but inclined to the femoral head axis and not perpendicular to the femoral head axis. The band of colour 418, 518 can be used to visually assess the orientation of the acetabular component 402, 502 relative to the pelvis as described in greater detail below.

In FIG. 12, the neck angle 430 between the longitudinal axis of the stem 432 and trial neck axis 416 is 135° and the angle of inclination of the acetabular cup is 45°. The coloured band 418 is tilted relative to the neck axis 416. With the trial joint reduced and the patient's hip joint in a neutral position, the plane of the mouth of the acetabular cup is parallel to the coloured band 418 indicating that the acetabular cup has been placed in the patient's pelvis at an angle of inclination of 45°.

The neutral position of the patient's hip joint can be defined as when the patient's leg is placed in an appropriate position to provide 0° of flexion/extension, 0° of abduction/adduction and 0° of internal/external rotation of the femur with respect to the pelvis. Also, the angle of rotation of the trial femoral head about the neck axis 416 is pre-determined, e.g. by a marking or some form of keying mechanism or clocking mechanism. The angle of inclination of the coloured band and angular position about the neck axis are selected such that, with the trial hip joint reduced and the trial hip joint in the neutral position, the plane of the mouth of the acetabular cup will be parallel to the coloured band 418, when the neck axis 416 has an anteversion angle of 15° relative to the femur and the acetabular cup has an anteversion angle of 20° and an inclination axis of 45° relative to the pelvis.

For a cup inclination angle of 45° and a neck angle 430 of 135°, the geometry is such, as illustrated in FIG. 1, that the left trial hip assembly 500 will have an exactly similar geometry to the right hip trial assembly 400. Hence, the same trial components can be used for the right trial hip joint 400 and also the left trial hip joint 500, except that the trial femoral head needs to be rotated by 180° about the trial neck axis 416, 516 between use for the left trial hip joint 500 and right trial hip joint 400.

Figure 13:
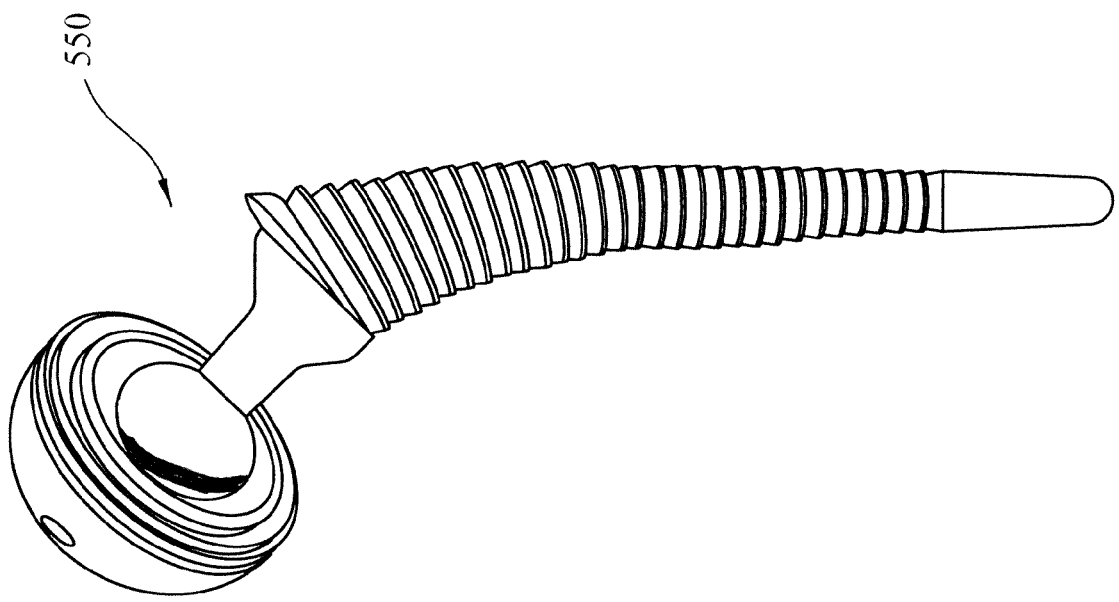
FIG. 13 shows a view of right and left hip trialling assemblies having a second geometry.
Figure 13:
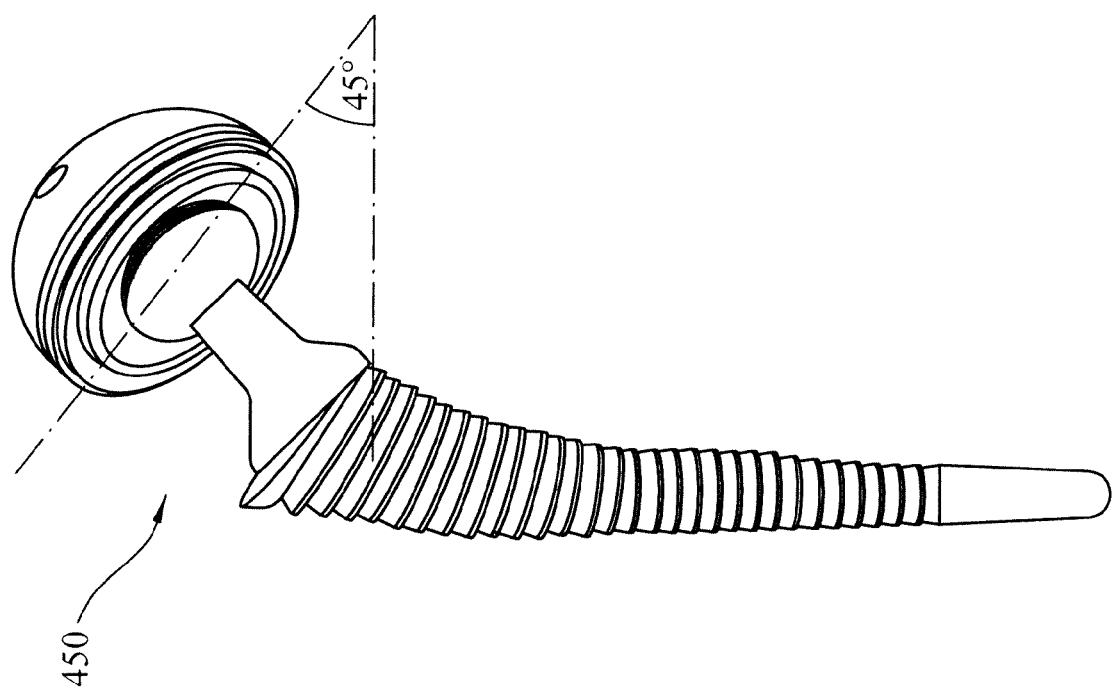

However, for some patients and/or procedures an acetabular cup inclination angle of 45° may not be appropriate. If the cup inclination angle is varied away from 45°, for example to 40°, then the approach illustrated in FIG. 12 will no longer work. For example, FIG. 13 shows a similar first right trial hip joint 450 and second left trial hip joint 550, but in which the band on the trial head is inclined such that for the right trial hip joint, with the trial hip joint in the neutral position, the plane of the mouth of the acetabular cup is parallel to the coloured band when the acetabular cup has an inclination angle of less, than 45°, for example 40°. In this case, if the trial femoral head is simply rotated by 180° about the neck axis before being attached to the trial neck for use in the left hip joint, then if the acetabular cup of the left hip joint is positioned with the correct target inclination of 40°, as illustrated by trial assembly 550 in FIG. 13, then the plane of its mouth will no longer be parallel with the coloured band, indicating incorrect orientation of the cup when that is not actually the case.

This can be avoided by using two different femoral trail heads one with the coloured band correctly positioned for a left hip joint and the other with the coloured band correctly positioned for a right hip joint. However, this would lead to an increase in inventory and instrumentation. This may also lead to the increased possibility of errors if a surgeon accidentally used a trial femoral head configured for a left hip joint on a right hip joint.

Alternatively, a single femoral trial head could be used to avoid the need for increased inventory and instrumentation and having multiple bands with a first band being used to assess the acetabular cup orientation for a right hip joint and a second band being used to assess the acetabular cup orientation of a left hip joint. However, this would make the surface of the trial head more visually complex and may require the surgeon to check or confirm which coloured band to use as the visual reference for a left hip or a right hip. Also, the coloured bands may need to overlap and so would obscure each other. Further, it may be harder to distinguish the different coloured bands in the surgical site if there is limited visibility, for example owing to the presence of other instrumentation and/or a small incision and/or blood or other bodily fluids or materials. Hence, a simpler visual indication which can be used to assess cup placement for both right and left hip joints may be beneficial.

FIG. 13 shows a perspective view of trialling apparatus 600 according to the invention and comprising a trial femoral neck 612 and a trial femoral head 614. The trial femoral neck 612 has a neck axis 616 extending along its longitudinal axis. The trial femoral neck 612 has a circular peg 652 extending from an under surface and a closed circular cylindrical bore 654 extending from the under surface and which can mate with corresponding respective female and male features on a upper surface of the broach 410 to releasably attach the trial neck to the broach in use. A superior lateral side 656 of the trial neck bears an indicium in the form of a line 658 extending along the middle of the width of the neck and parallel to the neck axis 616. Line 658 provides a visible datum which can be used to check the rotational position of the trial head 614 in use.

Trial neck 612 has a taper 660 toward a free end. A side wall of the taper has a groove 662 therein extending around the neck axis 616 and a C-ring or c-clip 564 is retained in groove 662. The C-ring may be made of any suitable compliant material, such as a rubber, silicone or metal. The use of a C-ring may be preferable when the material is less compliant, such as a metal, so as to help allow the C-ring to compress. The c-clip interacts between the taper and a corresponding groove extending around an interior wall of the trial head which defines the cavity 670. The c-clip and groove provide a retention mechanism by which the trial femoral head may be releasably attached to the trial neck.

In other embodiments, the retention mechanism may be provided in the form of a friction fit. For example, an O-ring of a suitable compliant material, such as a rubber or silicone or similar, may be provided in groove 662 in the taper so as to may interfere with a corresponding part of an inner wall of the trial head which defines the cavity 670.

Figure 15:
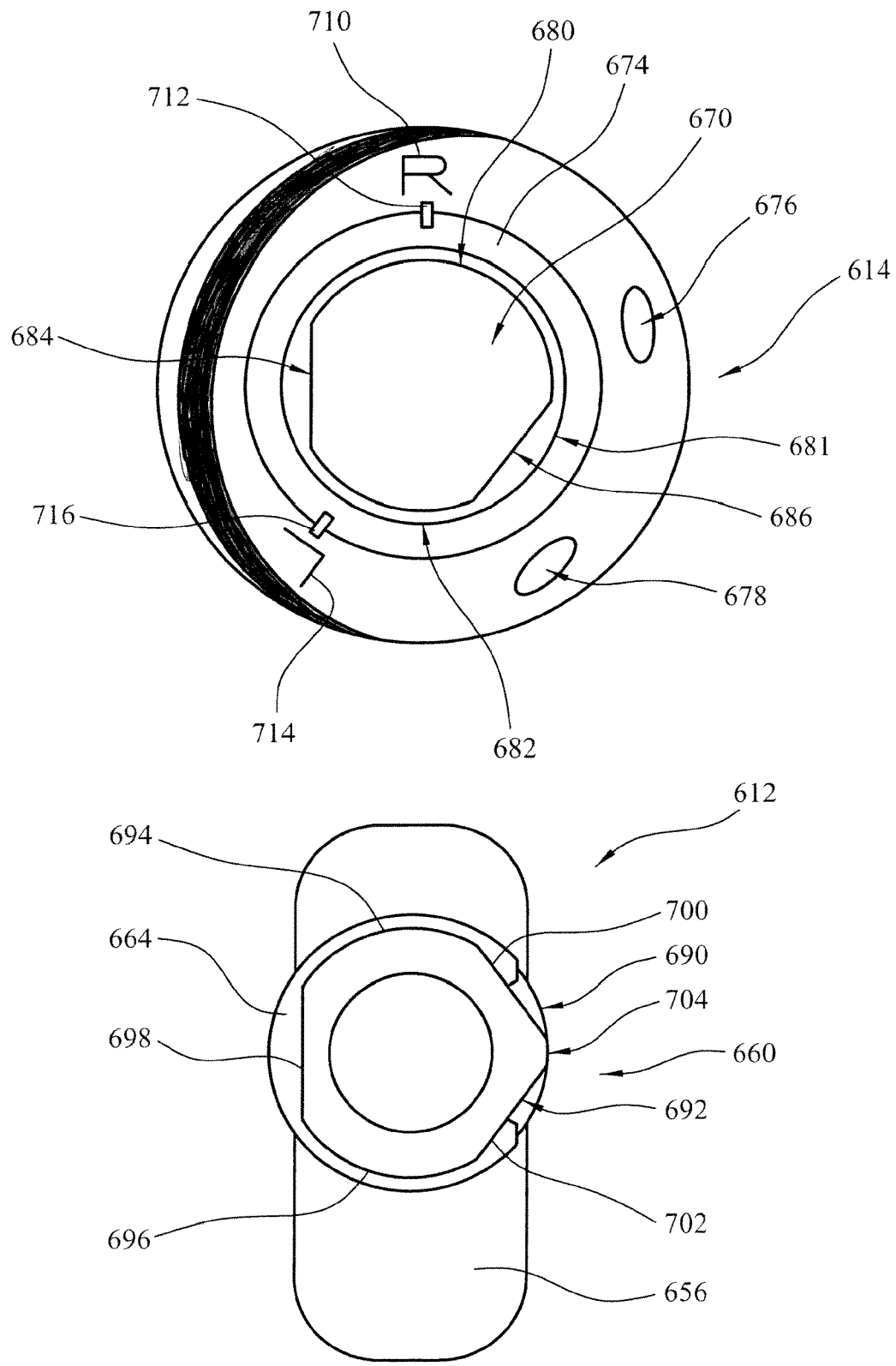
FIG. 15 shows end views of the trial femoral head and trial femoral neck of the kit of parts for assembly in a first right hip configuration.

The taper 660 has a complex shape as best illustrated by FIG. 15, which shows an end view of the trail neck along the trail neck axis 616.

The trial femoral head 614 has a generally truncated spherical shape and has a bore 670 extending along a trial head axis 672 which passes through a pole of the trail femoral head, through the centre of the spherical head and generally perpendicularly to the plane of the lower truncated portion defined by circular rim 674. The trial head axis 672 is co-linear with the trial neck axis 616 in FIG. 14. The outer surface of the trial femoral head also includes a first 676 and a second 678 recess or depression to increase a user's grip when manipulating the trial head, and positioned on generally the same side of the trial femoral head. These provide grip elements to facilitate removal of the trail femoral head from the trial femoral neck during use.

The outer surface of the trial femoral head includes a single indicium 618 in the form of a band having a colour different to the colour of the remainder of the outer surface. The coloured band 618 extends around an equator of the spherical head. The coloured band 618 is tilted or inclined relative to the trial head axis 672 in that the plane of the coloured band 618 is not perpendicular to the trial head axis 672. Also, the coloured band has an angular position of rotation about the trial head axis 672. The values of the angular positon of rotation and of tilt of the coloured band are selected to correspond to target values of anteversion and inclination of the acetabular cup. For example, if the target values of anteversion and inclination are 20° and 40°, then the band is tilted at an angle of about 31° away from parallel with the plane of the rim 674 and forming an acute angle of 59° with the trial head axis 672. The coloured band 618 has a width of about 3.5 mm. The lowest point of the coloured band is positioned approximately mid-way between the "L" and "R" indicia, as indicated by dashed line 711 in FIG. 15, and hence at an angle of approximately 72° about the trial head axis 672 relative to the "R" indicium. The trial head can be provided in a range of sizes, for example having diameters of approximately 28 mm, 32 mm and 36 mm, although other sizes may also be sued for other embodiments.

As also best illustrated in FIG. 15, which shows a view of the underside of the trial femoral head along the trial femoral head axis 672, an interior wall of the trial head defines the cavity 670. The interior wall has an outer portion 681 which defines an outer portion of the cavity which is circular, and an inner portion which defines an inner portion of the cavity which is non-circular. The outer portion 681 of the interior wall has a simple curved, circular form.

The inner portion of the interior wall has a plurality of different sections and includes rectilinear and curved sections. In particular, the interior wall has a first curved section 680, a second curved section 682, a first rectilinear section 684 and a second 686 rectilinear section. The first and second curved sections 680, 682 are on opposed sides of the cavity and the first and second rectilinear sections 684, 686 are on opposed sides of the cavity 670. The first curved section 680 extends over a greater angle than the second curved section 682 and consequently, the first 684 and second 686 rectilinear sections are not parallel.

The trial femoral head also includes an "R" 710 and a dash 712 which provide indicia providing a rotational position datum for the trial femoral head when being used to trial a right hip joint, "right markings". The "R" and dash indicia are provided adjacent the rim 674 of the trial femoral head at a first angular position. The trial femoral head further includes an "L" 714 and a further dash 716 which provide indicia providing a rotational position datum for the trial femoral head when being used to trial a left joint, "left markings". The "L" and dash indicia are provided adjacent the rim 674 of the trial femoral head at a second angular position. The obtuse angle about the rim 674 between the right and left markings, in the clockwise direction, is approximately 216°, and hence the acute angle in the anti-clockwise direction is approximately 144°.

Similarly, the taper at the free end 660 of the trial neck has an outer portion 690 and an inner portion 692. The outer portion of the taper wall has a curved, slightly tapering circular wall which is sized to fit snuggly within the outer portion of the trial head cavity.

An inner portion of the taper wall defines the inner portion 692 of the taper 660 and has a plurality of different sections and includes rectilinear and curved sections. In particular, the inner taper wall has a first curved section 694, a second curved section 696, a first rectilinear section 698, a second 700 rectilinear section and a third rectilinear section 702. The first and second curved sections 694, 696 are on opposed generally inferior and superior sides of the trial neck and the first rectilinear section 698 is on a generally posterior side of the trial neck generally opposed to the second and third rectilinear portions 700, 702 on a generally anterior side of the trial neck. The second and third rectilinear portions meet to define an apex 704.

Figure 14:
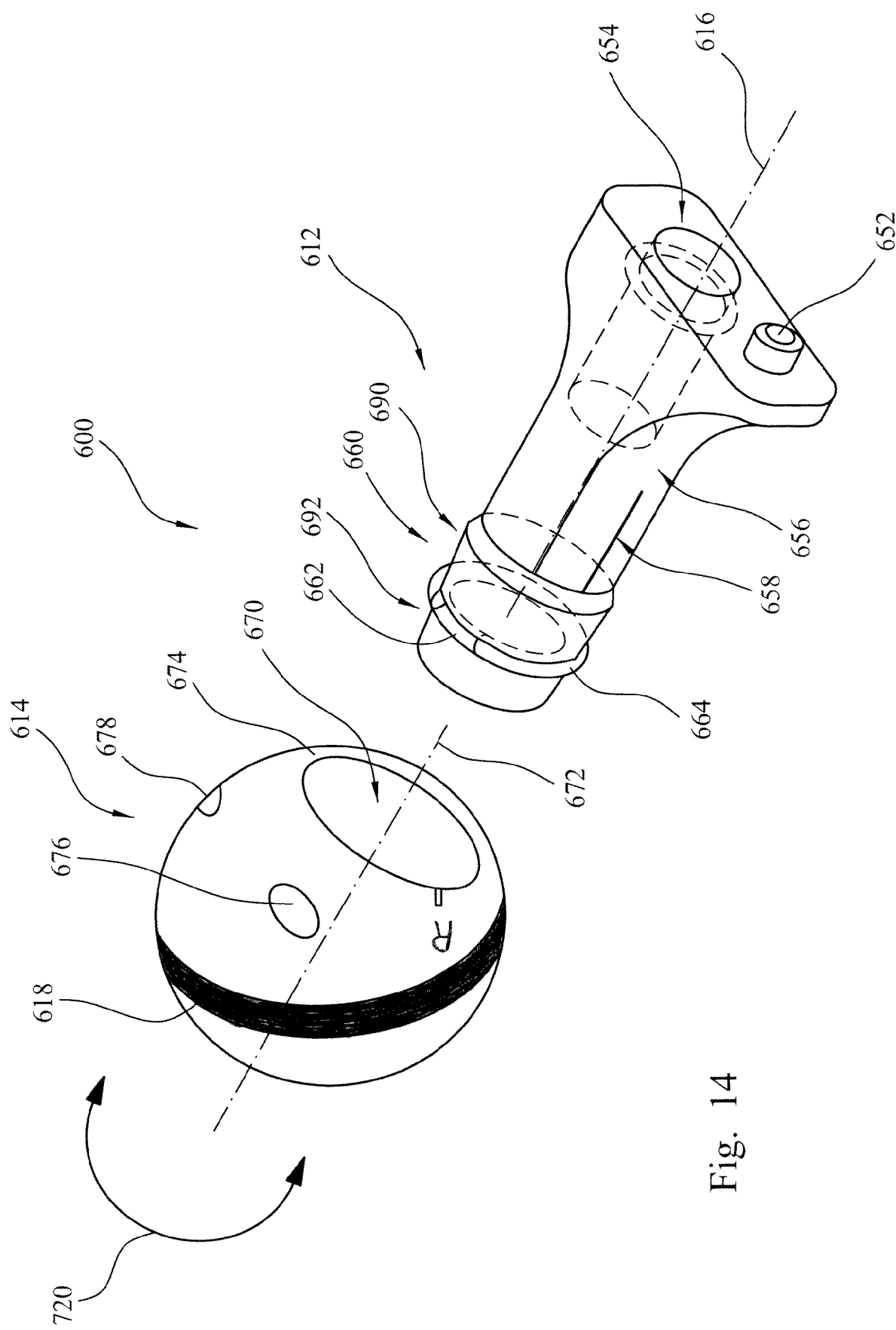
FIG. 14 shows a perspective view of a kit of parts according to the invention.

The rotational position of the trial head 614 in FIG. 15, corresponds to that also shown in FIG. 14, in which, when the taper 660 is fully engaged in the cavity 670, will result in the "R' and dash indicia being aligned with the line 658 on the superior surface 656 of the trial neck. In this right hip joint configuration, trial head cavity rectilinear wall portion 684 abuts taper rectilinear wall portion 698 and trial head cavity rectilinear wall portion 686 abuts taper rectilinear wall portion 700 thereby keying the angle of rotation of the trail femoral head about the trial neck axis 616. Circular C-ring 664 provides a friction fit with the outer, circular portion of the trail head cavity 670. In this first, right hip configuration, the trial head and trial neck assembly can be used to assess the orientation of an acetabular cup for a right hip joint in a manner similar to that described above with reference to FIGS. 12 and 13, but with target acetabular cup anteversion and inclination angles of 20° and 40° respectively, a femoral neck anteversion angle of 15° and with the hip joint in the neutral position.

Figure 16:
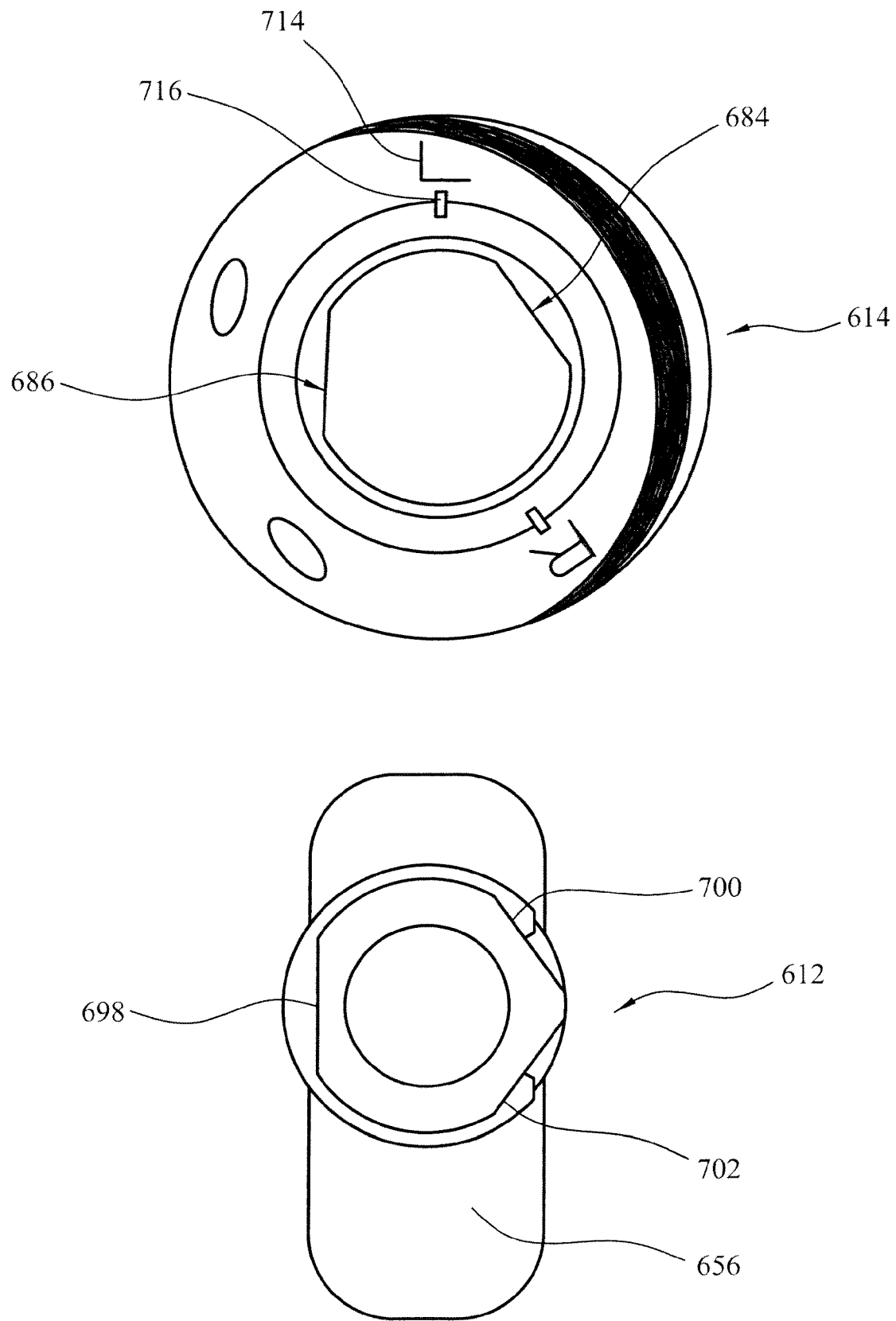
FIG. 16 shows end views of the trial femoral head and trial femoral neck of the kit of parts for assembly in a second left right hip configuration.

FIG. 16 shows a view of the trial femoral head 614 and trial neck 612 similar to that of FIG. 15, other than the trial femoral head having been rotated by 144° in a clockwise direction, or equivalently by 216° in an anticlockwise direction, about the trial head axis 672, as represented by curved doubled headed arrow 720 in FIG. 14.

The rotational position of the trial head 614 in FIG. 16 is such that when the taper 660 is fully engaged in the cavity 670, this will result in the "L" 714 and dash 716 indicia being aligned with the line 658 on the superior surface 656 of the trial neck. In this left hip joint configuration, trial head cavity rectilinear wall portion 586 abuts taper rectilinear wall portion 598 and trial head cavity rectilinear wall portion 684 abuts taper rectilinear wall portion 702 thereby keying the angle of rotation of the trail femoral head about the trial neck axis 616. Again, circular C-ring 664 provides a friction fit with the outer, circular portion of the trail head cavity. In this second, left hip configuration, the trial head and trial neck assembly can be used to assess the orientation of an acetabular cup for a left hip joint in a manner similar to that described above with reference to FIGS. 12 and 13, but with target acetabular cup anteversion and inclination angles of 20° and 40° respectively, a femoral neck anteversion angle of 15° and with the hip joint in the neutral position.

Hence, the same trial head 614 and trial neck 612 can be used to trial either, or both, a right hip and/or a left hip, with a simple visual indication on the trial head surface of the target orientation of the acetabular cup.

Figure 17:
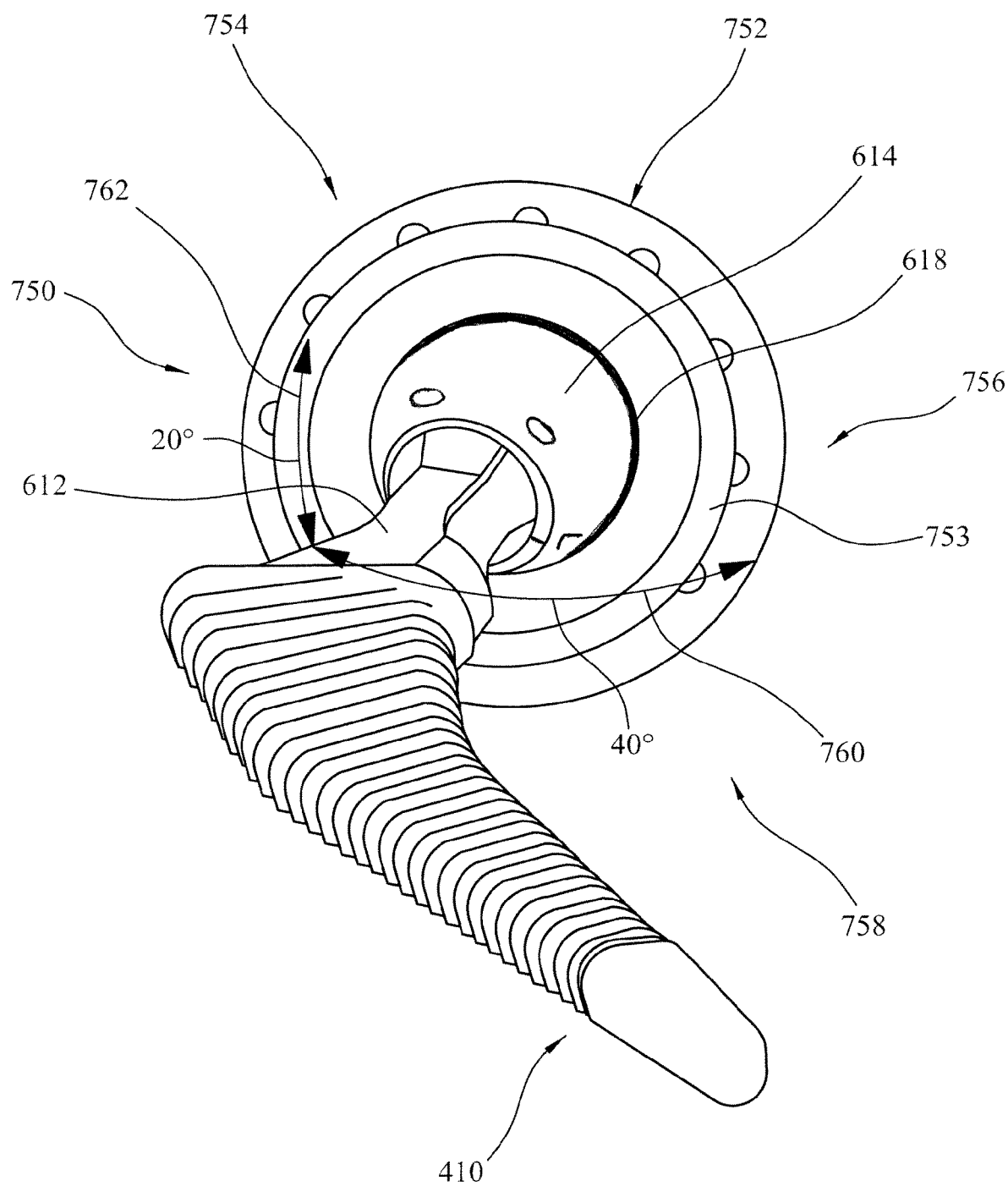
FIG. 17 shows a perspective view of a trialling assembly illustrating the neck anteversion, cup anteversion and cup inclination.

FIG. 17 illustrates the right hip joint trial assembly 750 when assembled according to FIG. 15 of the trail head 614 and trial neck 612, mounted on broach 410 and an optimally positioned acetabular cup 752 relative to the transverse plane 754, sagittal plane 756 and coronal plane 758 of a patient's pelvis and with the trial hip joint in a neutral position. As illustrated in FIG. 17, the cup 752 is inclined by an angle 760 of 40° relative to the transverse plane 754 and anteverted by an angle 762 of 20° relative to the coronal plane 758. The body of broach 410 is not co-planar with the coronal plane 758, but rather the trial neck axis subtends an angle of 15° with the coronal plane, corresponding to the neck axis being anteverted by 15° relative to the femur. The co-incidence of the coloured band 618 and the plane of the mouth of liner 753 of cup 752 provides a visual indication that the cup has been position with the target orientation of 20° cup anteversion, and 40° cup inclination. Also, the combined anteversion of the femoral component and cup component of the hip is approximately 35°.

As noted above, the inclination of the coloured band 618 relative to the trial head axis is approximately 30°. This provides a trial head suitable for a target cup orientation of 40° inclination and 20° anteversion, relative to the pelvis, and a 35° combined anteversion for radiographic angles. This facilitates the assessment of the positioning of the cup clinically by x-ray or other radiographic imaging of the APP. It will be noted, that in FIG. 17, the stem anteversion angle and the cup anteversion angle are not in the same plane and therefore the combined anteversion angle is not truly 35°. However, the stem anteversion angle and cup anteversion angles are equivalent in the anatomical coordinate system.

It will be appreciate that for other target angles of inclination of the acetabular cup, different angular separations between the left and right markings and angular positions of the rectilinear walls 684 and 686 of the trial head, and corresponding changes to the angular positions of the rectilinear walls 700 and 702 of the trial neck will be made. Generally speaking, as the target angle of inclination of the acetabular cup decreases from 45°, the angular separation between the left markings and right markings in a clockwise direction will decrease from 180°, and hence increase from 180° in an anti-clockwise direction. The angle of inclination of the band 618, angular position of the band 618 about the trial head axis, and the angular separation between the "L" and "R" indicia will also be varied accordingly.

Figure 18:
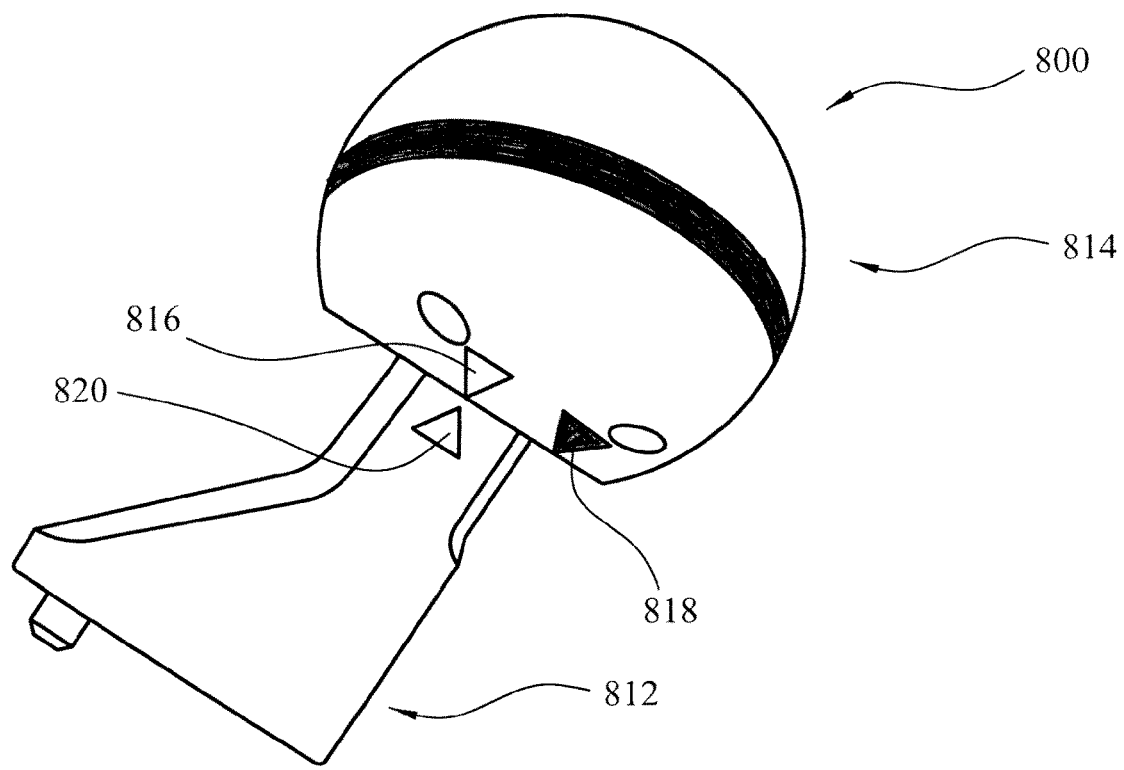
FIG. 18 shows a second embodiment of a right hip trialling assembly.
Figure 19:
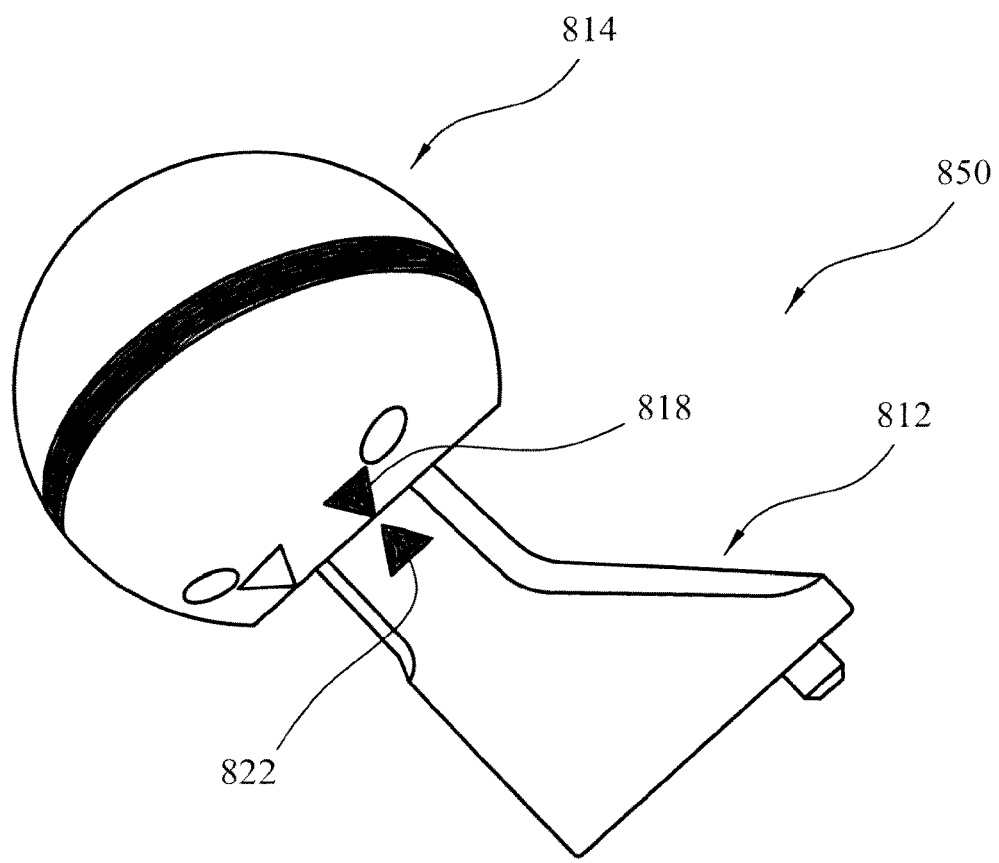
FIG. 19 shows the second embodiment as a left hip trialling assembly.

FIG. 18 shows a view in the anterior-posterior direction of a further embodiment of a trial assembly in a right hand hip configuration 800 and FIG. 19 shows a view in the anterior-posterior direction of the further embodiment of the trial assembly in a left hand hip configuration 850. The trial assembly includes a trail head 814 and a trial neck 812 similar to those described above. However, the trial head 814 and trail neck include 812 include different indicia which are differently positioned in order to facilitate ease of assembly of the trial head 814 and the trial neck 812 in the right hand 800 and left hand 850 hip configurations.

The trial head 814 includes a first 816 and a second 818 indicium which are visually dissimilar and are located adjacent the rim of the trail head and generally on an anterior side of the trial head in use. As illustrated, the first indicium 816 is in the form of a white triangle and the second indicium 818 is in the form of a black triangle. In other embodiments, the trial head indicia 816, 818 may have other shapes and colours, provided they are visually distinguishable from each other. The trail head indicia 816, 818 are angularly separated by approximately 36°.

The trial neck 812 includes a first 820 and a second 822 indicium which are visually dissimilar and are on opposed sides of the trial neck 812 corresponding to the anterior face for a right hand hip 800 and to the anterior face for a left hand hip 850 respectively. The trial neck indicia 820, 822 are positioned along the neck so as to be adjacent the rim of the trial head 814 when assembled. As illustrated, the first trial neck indicium 820 is in the form of a white triangle and the second trial neck 822 is in the form of a black triangle. In other embodiments, the trial neck indicia 820, 822 may have other shapes and colours, provided they are visually distinguishable from each other. However, the first trial head indicium 816 and the first trial neck indicium 820 are either visually related, similar or the same, and the second trial head indicium 818 and the second trial neck indicium 822 are either visually related, similar or the same.

Hence, during use, with the trial neck arranged for a right hand hip, as illustrated in FIG. 18, the white triangle 820 on the face of the trial neck visible anteriorly will be visible to the surgeon and can be used both to assist with angularly aligning the trial head 814, via its white triangle 816, and also, as the indicia 816, 820 are matching, provides visual feedback to the surgeon that the trial head 814 has been correctly assembled on the trial neck for a right hand hip. Similarly, with the trial neck arranged for a left hand hip, as illustrated in FIG. 19, the back triangle 822 on the face of the trial neck visible anteriorly will be visible to the surgeon and can be used both to assist with angularly aligning the trial head 814, via its black triangle 818, and also, as the indicia 818, 822 are matching, provides visual feedback to the surgeon that the trial head 814 has been correctly assembled on the trial neck 812 for a left hand hip.

As well as being able to use the same trial head and trail neck for either a left hip and/or a right hip, the trail neck 612, 812 and trial head 614, 814 have a number of other advantages. For example, as the trial taper has a circular inner portion, and the rectilinear wall portions 698, 700, 702 are effectively cut aways, a conventional trial femoral head with a simple tapered circular cavity can also be used with the trial neck 612. Hence, there is no need to provide an additional trial neck for use with conventional trial femoral heads. For further example, as the trial head has rectilinear wall portions 684, 686 in the inner portion of the trial head tapered cavity 670, a conventional trial neck with a conventional taper cannot properly be used as the trial head 614 would not fully seat on a conventional neck taper. Hence, the risk of a surgeon accidentally using the trial femoral head 614, 814 with a conventional trial neck is reduced.

Use of the trial neck 612, 812 and trial femoral head 614, 814 is generally as follows. After preparation of the femur, and with the final broad or reamer still in place, the reamer or broach handle is removed and the trial neck 612 is attached to the broach or reamer, with the superior surface 656 in a generally superior direction. After preparation of the acetabular cavity an acetabular cup, and optionally any liner, are inserted in the acetabular cavity at an orientation having angles of anteversion and inclination relative to the patient's pelvis. A trial femoral head 614, 814 having a diameter corresponding to the size of the acetabular cup, or liner, is then selected. It is determined whether the hip currently being replaced is a left hip or a right hip.

The trial femoral head 614 is then rotated to align the appropriate right 710, 712 or left 714, 716 indicia with the marking 658 on the trial neck and trial femoral head 614 is placed on the trial neck 616 until the trial femoral head is fully seated on the taper 660 and held in place by the friction fit provided by C-ring 664. Alternatively, the trial femoral head 814 is then rotated to align the appropriate right 816 or left 818 indicia with the matching marking 820 or 822 on the anterior face of the trial neck 812 and the trial femoral head 814 is placed on the trial neck 816 until the trial femoral head is fully seated on the taper 660 and held in place by the friction fit provided by C-ring 664.

The trial joint is then reduced and the hip placed in the neutral position described above and as illustrated in FIG. 17. The surgeon can then visually assess the orientation of the acetabular cup by comparing the orientation of the plane of the mouth of the acetabular cup or liner with the black band 618 on the surface of the trial femoral head. If the black band 618 is parallel with the mouth of the cup or the liner, then this indicates that the acetabular cup had been placed with the target orientation, being, in this example, anteversion and inclination angles of 20° and 40° respectively. The surgeon may use this information simply as real time feedback or may take further action, such as repositioning the acetabular cup and/or femoral components, if possible to try and improve the likely surgical outcome. The remainder of the surgical procedure is then largely conventional.

If a double hip replacement is being carried out, then at the same stage of the procedure on the other hip, the same trial neck 612, 812 and trial head 614, 814 can be used, but in the second configuration with the trial head rotated by 216° or 144° about the trial neck axis.

Hence, by controlling the angular rotation of the trial head 614, 814 about the trial neck axis 616, that is by rotating the head by a specific angle different to 180°, when flipping between right side and left side hips, the error shown in FIG. 13 can be corrected exactly. Therefore a single trial head 614, 814 with a single band 618 can be used for non-45° cup inclination angles and/or non-135° neck angle configurations. In the described embodiment, the trial components are configured for a 135° neck angle, target cup radiographic inclination and anteversion values of 40° and 20° respectively and 15° of assumed native femoral anteversion. In this case, the trial head rotation angle is approximately a 216° clockwise rotation from right to left sides. In other embodiments, the trial head rotation angle will vary depending on the values of the neck angle and/or cup inclination angle and/or cup anteversion angle and/or native femoral anteversion angle.

In the described embodiment of the trial head and trial neck angular position and rotation angle are controlled by a series of flats on both the inner portion of the cavity taper geometry of the trial head cavity and the upper-portion of the taper geometry of the neck. However, formations other than flats may be used to realise the keying behaviour described herein. The design is such that the trial head 614, 814 will only engage fully with the trial neck 612, 812 when rotated to be in the right-side hip configuration or left-side hip configuration. In one embodiment these two configurations are indicated by "R" and "L" letters on the trial head surface which can be aligned with the marker 658 on the superior, lateral side 656 of the trial neck to facilitate correct assembly of the femoral trial by the surgeon. In a further embodiment these two configurations are indicated by white and black triangles on the trial head surface which can be aligned with a respective one of white and black triangles on the anteriorly directed face of the trial neck to facilitate correct assembly of the femoral trial by the surgeon.

For alternative cup inclination and/or stem angle configurations, the flats geometry is simply modified to provide the appropriate angle of rotation for the right hand hip and left hand hip configuration angle.

Additionally, the described approach facilitates the use of conventional trial femoral heads being used with the trial neck 612, 812 and also prevents the trial head 614, 814 being used with conventional trial necks.

Various changes, modifications, substitutions and adaptations of the described embodiment will be apparent to the person of ordinary skill in the art from the above description.

The invention claimed is:

1. A femoral trialling kit for assessing acetabular cup orientation during a left hip joint surgical procedure and a right hip joint surgical procedure, comprising:
   a trial femoral head having an inner wall defining a cavity extending along a head axis and a visual alignment guide on an outer surface of the trial femoral head; and
   a trial femoral neck having a taper at a free end, the taper being receivable within the cavity, wherein one of the taper and the inner wall has a first anti-rotation feature and a second anti-rotation feature, the first anti-rotation feature and the second anti-rotation feature being inclined, and the other of the taper and the inner wall has a third anti-rotation feature, and wherein the trial femoral head is attachable to the trial femoral neck in a first angular configuration corresponding to a right hip joint, in which the third anti-rotation feature and the first anti-rotation feature engage, and a second angular configuration corresponding to a left hip joint, wherein the third anti-rotation feature and the second anti-rotation feature engage;
   wherein the visual alignment guide comprises a single indicium only and wherein the single indicium is in the form of a band having a first colour and wherein the surface of the trial head has a second colour and the first colour and the second colour are different colours.

2. The femoral trialling kit of claim 1, wherein the visual alignment guide has a width of at least 3 mm.

3. The femoral trialling kit of claim 1, wherein the trial femoral neck includes a neck indicium and the trial femoral head includes a first head indicium and a second head indicium on the outer surface of the trial femoral head and wherein the first head indicium and the second head indicium are respectively positioned about the head axis so that when the trial femoral head is attached to the trial femoral neck in the first angular configuration the second head indicium is aligned with the neck indicium and when the trial femoral head is attached to the trial femoral neck in the second angular configuration the first head indicium is aligned with the neck indicium.

4. The femoral trialling kit of claim 3, wherein the neck indicium is on a superior lateral surface of the trial femoral neck.

5. The femoral trialling kit of claim 1, and further including a retention mechanism arranged to releasably attach the trial femoral head to the taper.

6. The femoral trialling kit of claim 5, wherein the retention mechanism is configured to provide a friction fit between the taper and the cavity.

7. The femoral trialling kit of claim 5, wherein the retention mechanism includes a clip.

8. The femoral trialling kit of claim 1, wherein each anti-rotation feature is a flat surface.

9. The femoral trialling kit of claim 1, wherein the trial femoral head includes a first grip feature and/or a second grip feature in the outer surface.

10. The femoral trialling kit of claim 9, wherein the first grip feature and/or the second grip feature is in the form of a recess.

11. The femoral trialling kit of claim 1, wherein the visual alignment guide is positioned on the outer surface of the trial femoral head to correspond to an inclination angle of less than 45° of an acetabular cup in a pelvis of a patient, when the trial femoral head is mounted on the trial neck on a stem component within a femur of the patient with the trial hip joint reduced and in a neutral position.

12. The femoral trialling kit of claim 1, wherein the anti-rotation features are configured such that the trial femoral head is rotated by less than 180° in the first configuration compared to the second configuration.

* * * * *